(12) United States Patent
Andya et al.

(10) Patent No.: US 7,682,609 B2
(45) Date of Patent: *Mar. 23, 2010

(54) PROTEIN FORMULATION

(75) Inventors: James Andya, Milbrae, CA (US); Jeffrey L. Cleland, San Carlos, CA (US); Chung C. Hsu, Los Altos Hills, CA (US); Xanthe M. Lam, South San Francisco, CA (US); David E. Overcashier, Montara, CA (US); Steven J. Shire, Emerald Hills, CA (US); Janet Yu-Feng Yang, San Mateo, CA (US); Sylvia Sau-Yan Wu, San Francisco, CA (US)

(73) Assignee: Genentech, Inc., South San Franisco, CA (US)

( * ) Notice: Subject to any disclaimer, the term of this patent is extended or adjusted under 35 U.S.C. 154(b) by 551 days.

This patent is subject to a terminal disclaimer.

(21) Appl. No.: 11/441,994

(22) Filed: May 26, 2006

(65) Prior Publication Data

US 2006/0275306 A1 Dec. 7, 2006

Related U.S. Application Data

(60) Continuation of application No. 09/273,230, filed on Mar. 18, 1999, now abandoned, which is a division of application No. 08/615,369, filed on Mar. 14, 1996, now Pat. No. 6,267,958.

(60) Provisional application No. 60/029,182, filed on Jul. 27, 1995.

(51) Int. Cl.
    *A61K 39/395* (2006.01)
(52) U.S. Cl. .................................. 424/130.1
(58) Field of Classification Search ............ None
    See application file for complete search history.

(56) References Cited

U.S. PATENT DOCUMENTS

| | | | |
|---|---|---|---|
| 4,093,606 A | 6/1978 | Coval | |
| 4,165,370 A | 8/1979 | Coval | |
| 4,371,520 A | 2/1983 | Uemura et al. | |
| 4,439,421 A | 3/1984 | Hooper et al. | |
| 4,482,483 A | 11/1984 | Curry et al. | |
| 4,499,073 A | 2/1985 | Tenold | |
| 4,515,776 A | 5/1985 | Taniguchi et al. | |
| 4,597,966 A | 7/1986 | Zolton et al. | |
| 4,714,759 A | 12/1987 | Whitaker, Jr. | |
| 4,753,894 A | 6/1988 | Frankel et al. | |
| 4,816,567 A | 3/1989 | Cabilly et al. | |
| 4,835,257 A | 5/1989 | Friedrich-Fiechtl et al. | |
| 4,861,579 A | 8/1989 | Meyer et al. | |
| 4,877,608 A | 10/1989 | Lee et al. | |
| 4,891,319 A | 1/1990 | Roser | |
| 4,935,341 A | 6/1990 | Bargmann et al. | |
| 4,940,782 A | 7/1990 | Rup et al. | |
| 4,943,533 A | 7/1990 | Mendelsohn et al. | |
| 4,946,788 A | 8/1990 | Delespesse | |
| 4,962,035 A | 10/1990 | Leder et al. | |
| 4,968,603 A | 11/1990 | Slamon et al. | |
| 4,975,278 A | 12/1990 | Senter et al. | |
| 5,032,405 A | 7/1991 | Huang et al. | |
| 5,091,313 A | 2/1992 | Chang | |
| 5,096,885 A | 3/1992 | Pearlman et al. | |
| 5,149,653 A | 9/1992 | Roser | |
| 5,169,774 A | 12/1992 | Frankel et al. | |
| 5,183,884 A | 2/1993 | Kraus et al. | |
| 5,215,743 A | 6/1993 | Singh et al. | |
| 5,231,026 A | 7/1993 | Chang | |
| 5,252,467 A | 10/1993 | Chang | |
| 5,254,671 A | 10/1993 | Chang | |
| 5,260,416 A | 11/1993 | Chang | |
| 5,262,296 A | 11/1993 | Ogawa et al. | |
| 5,274,075 A | 12/1993 | Chang | |
| 5,288,477 A | 2/1994 | Bacus | |
| 5,292,867 A | 3/1994 | Chang | |
| 5,342,924 A | 8/1994 | Chang | |
| 5,359,046 A | 10/1994 | Capon et al. | |

(Continued)

FOREIGN PATENT DOCUMENTS

| | | |
|---|---|---|
| AU | B-30771/89 | 9/1989 |
| CA | 2138853 | 6/1995 |
| EP | 073371 | 3/1983 |
| EP | 0 173 494 A2 | 3/1986 |
| EP | 0 184 187 A2 | 6/1986 |
| EP | 196761 | 10/1986 |
| EP | 255249 | 2/1988 |
| EP | 263655 | 4/1988 |
| EP | 303746 | 2/1989 |
| EP | 317295 | 5/1989 |

(Continued)

OTHER PUBLICATIONS

Aasland et al., "Expression of Oncogenes in Thyroid Tumours: Coexpression of c-erbE2/neu and c-erbB" *British Journal of Cancer* 57(4):358-3963 (Apr. 1988).

(Continued)

*Primary Examiner*—Christopher H Yaen
(74) *Attorney, Agent, or Firm*—Atulya Agarwal, Esq.; Ginger R. Dreger, Esq.; Arnold & Porter LLP

(57) ABSTRACT

A stable lyophilized protein formulation is described which can be reconstituted with a suitable diluent to generate a high protein concentration reconstituted formulation which is suitable for subcutaneous administration. For example, anti-IgE and anti-HER2 antibody formulations have been prepared by lyophilizing these antibodies in the presence of a lyoprotectant. The lyophilized mixture thus formed is reconstituted to a high protein concentration without apparent loss of stability of the protein.

30 Claims, 10 Drawing Sheets

U.S. PATENT DOCUMENTS

| | | |
|---|---|---|
| 5,362,643 A | 11/1994 | Chang |
| 5,367,060 A | 11/1994 | Vandlen et al. |
| 5,399,670 A | 3/1995 | Bhattacharya et al. |
| 5,401,638 A | 3/1995 | Carney et al. |
| 5,410,025 A | 4/1995 | Moller et al. |
| 5,420,251 A | 5/1995 | Chang et al. |
| 5,422,258 A | 6/1995 | Chang |
| 5,428,133 A | 6/1995 | Chang |
| 5,449,760 A | 9/1995 | Chang |
| 5,464,751 A | 11/1995 | Greene et al. |
| 5,480,968 A | 1/1996 | Kraus et al. |
| 5,514,554 A | 5/1996 | Bacus |
| 5,543,144 A | 8/1996 | Chang |
| 5,571,894 A | 11/1996 | Wels et al. |
| 5,578,482 A | 11/1996 | Lippman et al. |
| 5,580,856 A | 12/1996 | Prestrelski et al. |
| 5,587,458 A | 12/1996 | King et al. |
| 5,589,167 A | 12/1996 | Cleland et al. |
| 5,604,107 A | 2/1997 | Carney et al. |
| 5,608,038 A | 3/1997 | Eibl et al. |
| 5,614,611 A | 3/1997 | Chang |
| 5,641,869 A | 6/1997 | Vandlen et al. |
| 5,654,403 A | 8/1997 | Smith et al. |
| 5,663,144 A | 9/1997 | Greene et al. |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A | 3/1998 | Hudziak et al. |
| 5,726,023 A | 3/1998 | Cheever et al. |
| 5,728,687 A | 3/1998 | Bissery |
| 5,747,261 A | 5/1998 | King et al. |
| 5,763,409 A | 6/1998 | Bayol et al. |
| 5,770,195 A | 6/1998 | Hudziak et al. |
| 5,772,997 A | 6/1998 | Hudziak et al. |
| 5,776,427 A | 7/1998 | Thorpe et al. |
| 5,783,186 A | 7/1998 | Arakawa et al. |
| 5,792,838 A | 8/1998 | Smith et al. |
| 5,801,005 A | 9/1998 | Cheever et al. |
| 5,821,337 A | 10/1998 | Carter et al. |
| 5,824,311 A | 10/1998 | Greene et al. |
| 5,834,229 A | 11/1998 | Vandlen et al. |
| 5,837,243 A | 11/1998 | Deo et al. |
| 5,837,523 A | 11/1998 | Greene et al. |
| 5,840,525 A | 11/1998 | Vandlen et al. |
| 5,846,538 A | 12/1998 | Cheever et al. |
| 5,849,700 A | 12/1998 | Sorensen et al. |
| 5,856,110 A | 1/1999 | Vandlen et al. |
| 5,859,206 A | 1/1999 | Vandlen et al. |
| 5,869,445 A | 2/1999 | Cheever et al. |
| 5,876,712 A | 3/1999 | Cheever et al. |
| 5,877,305 A | 3/1999 | Huston et al. |
| 5,908,835 A | 6/1999 | Bissery |
| 5,910,486 A | 6/1999 | Curiel et al. |
| 5,922,845 A | 7/1999 | Deo et al. |
| 5,939,531 A | 8/1999 | Wels et al. |
| 5,942,210 A | 8/1999 | Ultee et al. |
| 5,945,098 A | 8/1999 | Sarno et al. |
| 5,965,709 A | 10/1999 | Presta et al. |
| 5,977,322 A | 11/1999 | Marks et al. |
| 5,985,553 A | 11/1999 | King et al. |
| 6,015,567 A | 1/2000 | Hudziak et al. |
| 6,028,059 A | 2/2000 | Curiel et al. |
| 6,037,453 A | 3/2000 | Jardieu et al. |
| 6,054,297 A | 4/2000 | Carter et al. |
| 6,054,561 A | 4/2000 | Ring |
| 6,080,429 A | 6/2000 | Cleland et al. |
| 6,123,939 A | 9/2000 | Shawver et al. |
| 6,165,464 A | 12/2000 | Hudziak et al. |
| 6,267,958 B1 | 7/2001 | Andya et al. |
| 6,329,509 B1 | 12/2001 | Jardieu et al. |
| 6,685,940 B2 | 2/2004 | Andya et al. |
| 6,821,515 B1 | 11/2004 | Cleland et al. |
| 7,060,268 B2 | 6/2006 | Andya et al. |
| 2003/0202972 A1 | 10/2003 | Andya et al. |
| 2004/0197326 A1 | 10/2004 | Fick et al. |
| 2006/0099201 A1 | 5/2006 | Andya et al. |
| 2006/0275306 A1 | 12/2006 | Andya et al. |
| 2007/0020256 A1 | 1/2007 | Fick et al. |

FOREIGN PATENT DOCUMENTS

| | | |
|---|---|---|
| EP | 391444 | 10/1990 |
| EP | 0 531 539 A1 | 3/1993 |
| EP | 0 171 496 B1 | 5/1993 |
| EP | 589840 | 3/1994 |
| EP | 597101 | 5/1994 |
| EP | 0 599 274 A1 | 6/1994 |
| EP | 617127 | 9/1994 |
| EP | 648499 | 4/1995 |
| EP | 661060 | 7/1995 |
| EP | 841067 | 5/1998 |
| EP | 0 711 565 | 8/1998 |
| EP | 407392 | 10/1998 |
| EP | 616812 B1 | 11/1999 |
| JP | 59-44399 | 3/1984 |
| JP | 61-191622 | 8/1986 |
| JP | 61-194035 | 8/1986 |
| JP | 3-240498 | 10/1991 |
| JP | 5-65233 | 3/1993 |
| JP | 5-117165 | 5/1993 |
| JP | 5-170667 | 7/1993 |
| JP | 5-208918 | 8/1993 |
| JP | 5-213775 | 8/1993 |
| JP | 5-317084 | 12/1993 |
| JP | 95006982 B2 | 1/1995 |
| JP | 7-59588 | 3/1995 |
| JP | 7-206709 | 8/1995 |
| JP | 2761543 B2 | 6/1998 |
| JP | 2895105 B2 | 5/1999 |
| WO | WO 84/00890 | 3/1984 |
| WO | WO 86/01533 | 3/1986 |
| WO | WO 89/04834 | 6/1989 |
| WO | WO 89/06138 | 7/1989 |
| WO | WO 89/06692 | 7/1989 |
| WO | WO 89/09402 | 10/1989 |
| WO | WO 89/11297 | 11/1989 |
| WO | WO 90/11091 | 10/1990 |
| WO | WO 91/11456 | 8/1991 |
| WO | WO 92/10573 | 6/1992 |
| WO | WO 92/22653 | 12/1992 |
| WO | WO 93/04173 | 3/1993 |
| WO | WO 93/05799 | 4/1993 |
| WO | WO 93/12220 A1 | 6/1993 |
| WO | WO 93/19197 | 9/1993 |
| WO | WO 93/21232 A1 | 10/1993 |
| WO | WO 93/21319 A1 | 10/1993 |
| WO | WO 94/00136 A1 | 1/1994 |
| WO | WO 94/10202 | 5/1994 |
| WO | WO 94/22478 A1 | 10/1994 |
| WO | WO 94/28127 | 12/1994 |
| WO | WO 95/11009 | 4/1995 |
| WO | WO 95/15977 | 6/1995 |
| WO | WO 95/16051 | 6/1995 |
| WO | WO 95/17507 | 6/1995 |
| WO | WO 95/28485 | 10/1995 |
| WO | WO 96/18409 | 6/1996 |
| WO | WO 96/30046 | 10/1996 |
| WO | WO 97/04807 | 2/1997 |
| WO | WO 97/10004 | 3/1997 |
| WO | WO 97/20858 A1 | 6/1997 |
| WO | WO 97/27848 | 8/1997 |
| WO | WO 97/33616 | 9/1997 |
| WO | WO 97/38731 A1 | 10/1997 |

| WO | WO 97/45140 | 12/1997 |
| --- | --- | --- |
| WO | WO 98/22136 | 5/1998 |
| WO | WO 98/45479 A1 | 10/1998 |
| WO | WO 99/01556 | 1/1999 |

OTHER PUBLICATIONS

Adams and Weiner, "Intracellular single-chain Fv antibodies—a knockout punch for neoplastic cells?" *Gynecologic Oncology* 59(1):6-7 (Oct. 1995).

Arakawa et al., "Protein-Solvent Interactions in Pharmaceutical Formulations" *Pharmeceutical Research* 8(3):285-291 (1991).

Arboleda et al., "Effects of the 4D5 antibody on HER2/neu heterodimerization with other class I receptors in human breast cancer cells" *Proceedings of the American Association for Cancer Research* (Abstract #353) 37:51 (Mar. 1996).

Arteaga et al., "p185$^{c\text{-}erbB\text{-}2}$ Signaling Enhances Cisplatin-induced Cytotoxicity in Human Breast Carcinoma Cells: Association Between an Oncogenic Receptor Tyrosine Kinase and Drug-induced DNA Repair" *Cancer Research* 54(14):3758-3765 (Jul. 15, 1994).

Bacus et al., "Differentiation of Cultured Human Breast Cancer Cells (AU-565 and MCF-7) Associated With Loss of Cell Surface HER-2/neu Antigen" *Molecular Carcinogenesis* 3(6):350-362 (1990).

Bacus et al., "Tumor-inhibitory Monoclonal Antibodies to the HER-2/Neu Receptor Induce Differentiation of Human Breast Cancer Cells" *Cancer Research* 53(9):2580-2589 (May 1, 1992).

Bam et al., "Stability of Protein Formulations: Investigation of Surfactant Effects by a Novel EPR Spectroscopic Technique" *Pharm. Res.* 12:2-11 (1995).

Baselga and Mendelsohn, "Receptor Blockade With Monoclonal Antibodies As Anti-Cancer Therapy" *Pharmac. Ther.* 64:127-154 (1994).

Baselga et al., "Anti HER2 Humanized Monoclonal Antibody (MAb) Alone and in Combination with Chemotherapy Against Human Breast Carcinoma Xenografts" *Proeedings of ASCO-13th Annual Meeting*(Abstract #53), Dallas, TX 13:63 (Mar. 1994).

Baselga et al., "Monoclonal Antibodies Directed Against Growth Receptors Enhance the Efficacy of Chemotherapeutic Agents." *Annals of Oncology* (abstract #010) 5(Suppl. 5) (1994).

Baselga et al., "Phase II Study of Weekly Intravenous Recombinant Humanized Anti-P185$^{HER2}$ Monoclonal Antibody in Patients With HER2/neu-Overexpressing Metastatic Breast Cancer" *J. Clin. Oncol.* 14(13):737-744 (Mar. 1996).

Beauvais et al., "Both Glassy State and Native Structure are Required for Storage Stability of Lyophilized Interleukin-1 Receptor Antagonist" *Pharm. Res.* (Abstract #2007) 12(9):S-80 (1995).

Borst et al., "Oncogene Alterations in Endometrial Carcinoma" *Gynecologic Oncology* 38(3):364-366 (Sep. 1990).

Boulet et al., "Inhibitory Effects of an Anti-IgE Antibody E25 on Allergen-induced Early Asthmatic Response" *Am J Respir Crit Care Med* 155:1835-1840 (1997).

Burton et al., "Lyophilized hyperimmune equine serum as a source of antibodies for neonatal foals" *American Journal of Veterinary Research* 42(2):308-310 (Feb 1981).

Carraway and Cantley, "A Neu Acquaintance for ErbB3 and ErbB4: A Role for Receptor Heterodimerizaton in Growth Signaling" *Cell* 78:5-8 (Jul. 15, 1994).

Carter et al., "Humanization of an Anti-p185$^{HER2}$ Antibody For Human Cancer Therapy" *Proc. Natl. Acad. Sci. USA* 89(10):4285-4289 (May 1992).

Chang and Fischer, "Development of an Efficient Single-Step Freeze-Drying Cycle for Protein Formualtions" *Pharm. Res.* 12(6):831-837 (1995).

Chang et al., "Development of a Stable Freeze-dried Formulation of Recombinant Human Interleukin-1 Receptor Antagonist" *Pharmaceutical Research* 13(2):243-248 (1996).

Chang et al., "Surface-induced denaturation of proteins during freezing and its inhibition by surfactants" *Journal of Pharmaceutical Sciences* 85(12):1325-1330 (Dec. 1996).

Cleland and Jones, "Development of Stable Protein Formulations for Microencapsulation in Biodegradable Polymers" *Proceed. Intern. Symp. Control. Rel. Bioact. Mater.* 22:514-515 (1995).

Cleland et al., "Development of Stable Protein Formulations for Microencapsulation in Biodegradable Polymers" *Proceed. Intern. Symp. Control. Rel. Bioact. Mater.* 22:514-515 (1995).

Cleland et al., "The Development of Stable Protein Formulations: A Close Look at Protein Aggregation, Deamidation, and Oxidation" *Critical Reviews in Therapeutic Drug Carrier Systems* 10(4) :307-377 (1993).

Cohen et al., "Expression Pattern of the neu (NGL) Gene-Encoded Growth Factor Receptor Protein (p185$_{neu}$) in Normal and Transformed Epithelial Tissues of the Digestive Tract" *Oncogene* 4(1):81-88 (Jan. 1989).

Combs et al., "Comparative efficacy of Herceptin in the nude mouse tumor xenograft model: IV bolus versus subcutaneous infusion" (Poster presented at the Nov. 1999 AAPS National Meeting) (1999).

D'Souza and Taylor-Papadimitriou., "Overexpression of ERBB2 in Human Mammary Epithelial Cells Signals Inhibition of Transcription of the E-Cadherin Gene" *Proc. Natl. Acad. Sci. USA* 91(15):7202-7206 (Jul. 19, 1994).

Darzynkiewicz et al., "Features of apoptotic cells measured by (1992) flow cytometry" *Cytometry* 13(8):795-808 (1992).

De Santes et al., "Radiolabeled Antibody Targeting of the HER-2/neu Oncorprotein" *Cancer Research* 52:1916-1923 (1992).

Deshane et al., "Intracellular antibody against erbB-2 mediates targeted tumor cell eradication by apoptosis" *Cancer Gene Therapy* 3(2):89-98 (Mar.-Apr. 1996).

Deshane et al., "Intracellular antibody knockout of the ERBB2 oncoprotein achieves targeted eradication of tumor targets by induction of apoptosis" *Journal of Investigative Medicine* 43(Suppl. 2):328A (1995).

Deshane et al., "Targeted eradication of ovarian cancer mediated by intracellular expression of anti-erbB-2 single-chain antibody" *Gynecologic Oncology* 59(1):8-14 (Oct. 1995).

Deshane et al., "Targeted tumor killing via an intracellular antibody against erbB-2" *Journal of Clinical Investigation* 96(6):2980-2989 (Dec. 1995).

Deshane et al., "Transductional Efficacy and Safety of an Intraperitoneally Delivered Encoding an Anti-erbB-2 Intracellular Single-Chain Antibody for Ovarian Cancer Gene Therapy" *Gynecologic Oncology* 64(3):378-385 (Mar. 1997).

Digiesi et al., "Production and characterization of murine mAbs to the extracellular domain of human neu product GP185$^{HER2}$" *Hybridoma* 11(4):519-527 (Aug. 1992).

Draber et al., "Stability of Monoclonal IgM Antibodies Freeze-Dried in the Presence of Trehalose" *Journal of Immunological Methods* 181(1):37-43 (1995).

Drebin et al., "Down-Modulation of an Oncogene Protein Product and Reversion of the Transformed Phenotype by Monoclonal Antibodies" *Cell* 41(3):695-706 (Jul. 1985).

Drebin et al., "Inhibition of Tumor Growth by a Monoclonal Antibody Reactive With an Oncogene-Encoded Tumor Antigen" *Proc. Natl. Acad. Sci.* 83:9129-9133 (Dec. 1986).

Drebin et al., "Monoclonal Antibodies Reactive With Distinct Domains of the neu Oncogene-Encoded p185 Molecule Exert Synergistic Anti-Tumor Effects in Vivo" *Oncogene* 2:273-277 (1988).

Drebin et al., "Monoclonal Antibodies Specific for the neu Oncogene Product Directly Mediate Anti-tumor Effects In Vivo" *Oncogene* 2(4):387-394 (1988).

Fahy et al., "The Effect of an Anti-IgE Monoclonal Antibody on the Early- and Late-Phase Responses to Allergen Inhalation in Asthmatic Subjects" *Am J Respir Crit Care Med* 155:1828-1834 (1997).

Fendly, B.M. et al., "Characterization of Murine Monoclonal Antibodies Reactive to Either the Human Epidermal Growth Factor Receptor or HER2/neu Gene Product" *Cancer Research* 50:1550-1558 (Mar. 1, 1990).

Fraker and Speck Jr., "Protein and cell membrane iodinations with a sparingly soluble chloroamide, 1,3,4,6-tetrachloro-3a,6a-diphenylglycoluril" *Biochemical & Biophysical Research Communications* 80(4):849-857 (1978).

Fukushige et al., "Localization of a Novel v-erbB-Related Gene, c-erbB-2, on Human Chromosome 17 and Its Amplification in a Gastric Cancer Cell Line" *Molecular & Cellular Biology* 6(3):955-958 (Mar. 1986).

(Genentech, Inc. Proposal Request and Material Transfer Agreement with Richard H. Scheuermann (1993), 3 pages, and letters in relation to it dated Jun. 23, 1993 and Oct. 20, 1993).

Grim et al., "The level of erbB2 expression predicts sensitivity to the cytotoxic effects of an intracellular anti-erbB2 sFv" *Journal of Molecular Medicine* 76(6):451-458 (May 1998).

Groenen et al., "Structure-Function Relationships for the EGT/TGF-α Family of Mitogens" *Growth Factors* 11:235-257 (1994).

Guerin et al., "Overexpression of Either c-myc or c-erbB-2/neu Proto-Oncogenes in Human Breast Carcinomas: Correlation with Poor Prognosis" *Oncogene Res.* 3:21-31 (1988).

Guy et al., "Expression of the neu Protooncogene in the Mammary Epithelium of Transgenic Mice Induces Metastatic Disease." *Proc. Natl. Acad. Sci. USA* 89(22):10578-10582 (Nov. 15, 1992).

Haak-Frendscho et al., "Administration of an anti-IgE antibody inhibits CD23 expression and IgE production in vivo" *Immunology* 82:306-313 (1994).

Hancock et al., "A Monoclonal Antibody Against the c-erbB-2 Protein Enhances the Cytotoxicity of cis-Diamminedichloroplatinum Against Human Breast and Ovarian Tumor Cell Lines" *Cancer Research* 51:4575-4580 (Sep. 1, 1991).

Harwerth et al., "Monoclonal Antibodies Against the Extracellular Domain of the erbB-2 Receptor Function as Partial Ligand Agonists" *Journal of Biological Chemistry* 267(21):15160-15167 (Jul. 25, 1992).

"Herceptin (Trastuzumab)" *Product Information* (2000).

Hudziak et al., "Increased Expression of the Putative Growth Factor Receptor p185$^{HER2}$ Causes Transformation and Tumorigenesis of NIH 3T3 Cells" *Proc. Natl. Acad. Sci. USA* 84(20):7159-7163 (Oct. 1987).

Hudziak et al., "p185$^{HER2}$ Monoclonal Antibody Has Antiproliferative Effects In Vitro and Sensitizes Human Breast Cells to Tumor Necrosis Factor" *Molecular & Cellular Biology* 9(3):1165-1172 (Mar. 1989).

Hynes and Stern, "The Biology of erbB-2/neu/Her-2 and Its Role in Cancer" *Biochimica et Biophysica Acta* 1198(2-3):165-184 (Dec. 30, 1994).

Ilgen et al., "Characterization of anti-HER/2 antibodies which inhibit the growth of breast tumor cells in vitro" *Proceedings of the American Association for Cancer Research* (abstract #3209) 37:470 (Mar. 1996).

Ilgen et al., "Characterization of anti-HER/2 monoclonal antibodies which inhibit the growth of breast cancer cell lines in vitro" *Proceedings of the American Association for Cancer Research* (Abstract #564) 38:84 (Mar. 1997).

"Immune Globulin Intravenous (Human) Sandoglobulin" *Product Information, Physicians' Desk Reference* pp. 2075-2077 (1994).

"Iveegam", "Product Information, Immuno U.S., Inc." pps. 2 pages (1992).

Izutsu et al., "The effects of additives on the stability of freeze-deried β-galactosidase stored at elevated temperature" *Intl. J. Pharmaceutics* 71:137-146 (1991).

Kasprzyk et al., "Therapy of an Animal Model of Human Gastric Cancer Using a Combination of Anti-erbB-2 Monoclonal Antibodies" *Cancer Research* 52(10):2771-2776 (May 15, 1992).

Kern et al., "Inhibition of human lung cancer cell line growth by an anti-p185HER2 antibody" *American Journal of Respiratory Cell & Molecular Biology* 9(4):448-454 (Oct. 1993).

Kern et al., "p185$^{neu}$ Expression in Human Lung Adenocarcinomas Predicts Shortened Survival" *Cancer Research* 50(16):5184-5191 (Aug. 15, 1990).

King et al., "Amplification of a Novel v-erbB-Related Gene in a Human Mammary Carcinoma" *Science* 229:974-976 (Sep. 1985).

Kita et al., "ErbB receptor activation, cell morphology changes, and apoptosis induced by anti-Her2 monoclonal antibodies" *Biochemical & Biophysical Research Communications* 226(1):59-69 (Sep. 4, 1996).

Klapper et al., "A Subclass of Tumor-Inhibitory Monoclonal Antibodies to ErbB-2/HER2 Blocks Crosstalk With Growth Factor Receptors" *Oncogene* 14:2099-2109 (1997).

Kotts et al., "Differential Growth Inhibition of Human Carcinoma Cells Exposed to Monoclonal Antibodies Directed against the Extracellular Domain of the HER2/ERBB2 Protooncogene" In Vitro (Abstract #176) 25(3):59A (1990).

Kotts et al., "Differential Growth Inhibition of Human Carcinoma Cells Exposed to Monoclonal Antibodies Directed Against the Extracellular Domain of the HER2/ERBB2 Protooncogene" (poster presented at the Annual Meeting of the Tissue Culture Association held in Houston, Texas on Jun. 1990) pp. 1-13.

Kotts et al., "Growth Inhibition of Human Breast Carcinoma Cells Exposed to Combinations of Interferon-Gamma and Monoclonal Antibodies Directed Against the Extracellular Domain of the Her2/erbB2 Oncogene Protein" *FASEB Journal* (abstract #1470) 4(7):A1946 (1990).

Kumar et al., "Regulation of Phosphorylation of the c-erbB-2/HER2 Gene Product by a Monoclonal Antibody and Serum Growth Factor(s) in Human Mammary Carcinoma Cells" *Molecular & Cellular Biology* 11(2):979-986 (Feb. 1991).

Lee et al., "Transforming Growth Factor α: Expression, Regulation, and Biological Activities" *Pharmacological Reviews* 47(1):51-85 (Mar. 1995).

Lemke,G., "Neuregulins in Development" *Molecular and Cellular Neurosciences* 7:247-262 (1996).

Levi et al., "The Influence of Heregulins on Human Schwann Cell Proliferatin" *J. Neurosience* 15(2):1329-1340 (Feb. 1995).

Lewis et al., "Differential Responses of Human Tumor Cell Lines to Anti-p185$^{HER2}$ Monoclonal Antibodies" *Cancer Immunol. Immunother.* 37:255-263 (1993).

Lewis et al., "Growth Regulation of Human Breast and Ovarian Tumor Cells by Heregulin: Evidence for the Requirement of ErbB2 as a Critical Component in Mediating Heregulin Responsiveness" *Cancer Research* 56:1457-1465 (Mar. 15, 1996).

Maier et al., "Requirements for the Internalization of a Murine Monoclonal Antibody Directed against the HER-2/neu Gene Product c-erbB-2" *Cancer Research* 51(19):5361-5369 (Oct. 1, 1991).

Manning et al., "Stability of Protein Pharmaceuticals" *Pharm. Res.* 6(11):903-918 (1989).

Marth et al., "Effects of interferons on the expression of the proto-oncogene HER-2 in human ovarian carcinoma cells" *International Journal of Cancer* 50(1):64-68 (Jan. 2, 1992).

Masui et al., "Growth Inhibition of Human Tumor Cells in Athymic Mice by Anti-Epidermal Growth Factor Receptor Monoclonal Antibodies" *Cancer Research* 44(3):1002-1007 (Mar. 1984).

Masuko et al., "A murine Monoclonal Antibody That Recognizes an Extracellular Domain of the Human c-erbB-2 Protooncogene Product" *Jpn J. Cancer Res.* 80:10-14 (Jan. 1989).

McCann et al., "c-erbB-2 Oncoprotein Expression in Primary Human Tumors" *Cancer* 65(1):88-92 (Jan. 1, 1990).

McKenzie et al., "Generation and Characterization of Monoclonal Antibodies Specific for the Human neu Oncogene Product, p185" *Oncogene* 4:543-548 (1989).

Mendelsohn et al., "Receptor Blockade and Chemotherapy: A New Approach to Combination Cancer Therapy." *Annals of Oncology* (abstract #040) 7(Suppl. 1):22 (1996).

Moore et al., "Apoptosis in CHO Cell Batch Cultures: Examination by Flow Cytometry" *Cytotechnology* 17:1-11 (1995).

Morrissey et al., "Axon-Induced Mitogenesis of Human Schwann Cells Involves Heregulin and p185$^{erbB2}$" *Proc. Natl. Acad. Sci. USA* 92.:1431-1435 (Feb. 1995).

Myers et al., "Biological Effects of Monoclonal Antireceptor Antibodies Reactive with neu Oncogene Product, p185neu" *Methods in Enzymology* 198:277-290 (1991).

Natali et al., "Expression of the p185 encoded by HER2 oncogene in normal and transformed human tissues" *International Journal of Cancer* 45(3):457-461 (Mar. 15, 1990).

Nielsen et al., "p53 protein and c-erbB-2 protein (p185) expression endometrial adenocarcinoma of endometrioid type. An immunohistochemical examination on paraffin sections" *American Journal of Clinical Pathology* 102(1):76-79 (Jul. 1994).

Nielsen, et al., "Stability of Freeze Dried Horseradish Peroxidase Conjugated Monoclonal Antibodies Used in Diagnostic Serology" *Journal of Immunoassay* 16(2):183-197 (1995).

Nitta et al., "Preliminary trial of specific targeting therapy against malignant glioma" *Lancet* 335(8686):368-371 (Feb. 17, 1990).

Norton, L., "Evolving Concepts in the Systemic Drug Therapy of Breast Cancer." *Seminars in Oncology* 24(4 Suppl 10):S10-3-S10-10 (Aug. 1997).

Ohnishi et al., "Prolonged survival of mice with human gastric cancer treated with an anti-c-ErbB-2 monoclonal antibody" *British Journal of Cancer* 71(5):969-973 (May 1995).

Park et al., "Amplification, Overexpression, and Rearrangement of the erbB-2 Protooncogene in Primary Human Stomach Carcinomas" *Cancer Research* 49(23):6605-6609 (Dec. 1, 1989).

Pearlman et al., "Analysis of Protein Drugs" *Peptide and Protein Drug Delivery*, Vincent H. L. Lee, Marcel Dekker, Inc., Chapter 6, pp. 247-301 (1991).

Picker et al., "Control of lymphocyte recirculation in man. I. Differential regulation of the peripheral lymph node homing receptor L-selectin on T cells during the virgin to memory cell transition" *Journal of Immunology* 150(3):1105-1121 (Feb. 1, 1993).

Pietras et al., "Antibody to HER-2/neu Receptor Blocks DNA Repair After Cisplatin in Human Breast and Ovarian Cancer Cells" *Oncogene* 9:1829-1838 (1994).

Pikal et al., "The Effects of Formulation Variables on the Stability of Freeze-Dried Human Growth Hormone" *Pharm. Res.* 8:427-436 (1991).

Pikal, M., "Freeze-Drying of Proteins, Part 2: Formulation Selection" *Biopharm.* 3(9):26-30 (1990).

Plowman et al., "Heregulin Induces Tyrosine Phosphorylation of HER4/p180$^{erbH4}$" *Nature* (Letters to Nature) 366:473-475 (Dec. 2, 1993).

Plowman et al., "Ligand-Specific Activation of HER4/p180$^{erbB4}$, A Fourth Member of the Epidermal Growth Factor Receptor Family" *Proc. Natl. Acad. Sci. USA* 90:1746-1750 (Mar. 1993).

Press et al., "Expression of the HER-2/neu proto-oncogene in normal human adult and fetal tissue" *Oncogene* 5:953-962 (1990).

Presta et al., "Humanization of an Antibody Directed Against IgE" *J. Immunol.* 151(5):2623-2632 (Sep. 1, 1993).

Price et al., "Tumorigenicity and metastasis of human breast carcinoma cell lines in nude mice" *Cancer Research* 50(3):717-721 (Feb. 1, 1990).

Ravdin and Chamness, "The c-erbB-2 proto-oncogene as a prognostic and predictive maker in breast cancer: a paradigm for the development of other macromolecular markers—a review" *Gene* 159(1):19-27 (Jun. 14, 1995).

Ressing et al., "The influence of sucrose, dextran, and hydroxypropyl-/142-cyclodextrin as lyoprotectants for a freeze-dried mouse IgG$_{2a}$ monoclonal antibody (MN12)" *Pharmaceutical Research* 9(2):266-270 (1992).

Ring et al., "Distribution and Physical Properties of BCA200, a $M_r$ 200,000 Glycoprotein Selectively Associated with Human Breast Cancer" *Cancer Research* 49:3070-3080 (Jun. 1, 1989).

Ring et al., "Identity of BCA200 and c-erbB-2 Indicated by Reactivity of Monoclonal Antibodies with Recombinant c-erbB-2" *Molecular Immunology* 28(8):915-917 (1991).

Rodeck et al., "Interactions between growth factor receptors and corresponding monoclonal antibodies in human tumors" *J. Cellular Biochem.* 35(4):315-320 (1987).

Roy et al., "The Effects of Formulation and Moisture on the Stability of a Freeze-Dried Monclonal Antibody—Vinca Conjugate: A Test of the WLF Glass Transition Theory" *DNA and Cell Biology* 74:323-340 (1991).

"Sandoglobulin" *Physicians' Desk Reference* pp. 1965-1966 (1991).

Sarup et al., "Characterization of an Anti-P185$^{HER2}$ Monoclonal Antibody that Stimulates Receptor Function and Inhibits Tumor Cell Growth" *Growth Regulation* 1:72-82 (1991).

Sato et al., "An immunohistologic evaluation of C-erbB-2 gene product in patients with urinary bladder carcinoma" *Cancer* 70(10):2493-2498 (Nov. 15, 1992).

Scheuermann, R., "Anti-HER2 Effects" (slide which may have been (but was probably not) presented at a seminar by Scheuermann at Syntex on Aug. 3, 1994).

Schlom, J., "Monoclonal Antibodies: They're More and Less Than You Think" *Molecular Foundations of Oncology*, Broder, S. ed., Baltimore, MD:Williams & Wilkins, Chapter 6, pp. 95-134 (1991).

Scott et al., "p185$^{HER2}$ Signal Transduction in Breast Cancer Cells" *Journal of Biological Chemistry* 266(22):14300-14305 (Aug. 5, 1991).

Shawver et al., "Ligand-Like Effects Induced by Anti-c-erbB-2 Antibodies Do Not Correlate with and Are Not Required for Growth Inhibition of Human Carcinoma Cells" *Cancer Research* 54(5):1367-1373 (Mar. 1, 1994).

Shepard et al., "Monoclonal Antibody Therapy of Human Cancer: Taking the HER2 Protooncogene to the Clinic" *J. Clin. Immunol.* 11(3):117-127 (1991).

Slamon et al., "Human Breast Cancer: Correlation of Relapse and Survival with Amplification of the HER-2/neu Oncogene" *Science* 235:177-182 (Jan. 9, 1987).

Slamon et al., "Studies of the HER-2/neu Proto-Oncogene in Human Breast and Ovarian Cancer" *Science* 244:707-712 (May 12, 1989).

Sliwkowski et al., "A humanized monoclonal antibody for the treatment of HER2 overexpressing breast cancer" *Proceedings of the American Association for Cancer Research* (abstract only) 37:625-626 (Mar. 1996).

Sliwkowski et al., "Coexpression of erbB2 and erbB3 Proteins Reconstitutes a High Affinity Receptor for Heregulin" *Journal of Biological Chemistry* 269(20):14661-14665 (May 20, 1994).

Stancovski et al., "Mechanistic Aspects of the Opposing Effects of Monoclonal Antibodies to the ERBB2 Receptor on Tumor Growth" *Proc. Natl. Acad. Sci. USA* 88(19):8691-8695 (Oct. 1, 1991).

Tagliabue et al., "Selection of Monoclonal Antibodies Which Induce Internalization and Phosphorylation of p185$^{HER2}$ and Growth Inhibition of Cells With HER2/NEU Gene Amplification" *International Journal of Cancer* 47(6):933-937 (Apr. 1, 1991).

Tokuda et al., "In vitro and in vivo anti-tumour effects of a humanised monoclonal antibody against c-erbB-2 product" *British Journal of Cancer* 73(11):1362-1365 (Jun. 1996).

Trauth et al., "Monoclonal antibody-mediated tumor regression by induction of apoptosis" *Science* 245:301-305 (1989).

Valone et al., "Clinical trials of bispecific antibody MDX-210 in women with advanced breast or ovarian cancer that overexpresses HER-2/neu" *Journal of Hematotherapy* 4(5):471-475 (Oct. 1995).

Vitetta and Uhr, "Monoclonal Antibodies as Agonists: An Expanded Role for Their Use in Cancer Therapy" *Cancer Research* 54(20):5301-5309 (Oct. 15, 1994).

Vollmers et al., "Apoptosis of stomach carcinoma cells induced by a human monoclonal antibody" *Cancer* 76(4):550-558 (Aug. 15, 1995).

Wang et al., "Parenteral Formulations of Proteins and Peptides: Stability and Stabilizers" *J. Parenteral Sci. Tech.* (Technical Report No. 10) 42(2S):S4-S26 (1988).

Weiner et al., "Expression of the neu Gene-encoded Protein (P185$^{neu}$) in Human Non-Small Cell Carcinomas of the Lung" *Cancer Research* 50(2):421-425 (Jan. 15, 1990).

Weller et al., "Anti-Fas/APO-1 antibody-mediated apoptosis of cultured human glioma cells. Induction and modulation of sensitivity by cytokines" *Journal of Clinical Investigation* 94(3):954-964 (Sep. 1994).

Williams et al., "Expression of c-erbB-2 in Human Pancreatic Adenocarcinomas" *Pathobiology* 59(1):46-52 (1991).

Wright et al., "An intracellular anti-erbB-2 single-chain antibody is specifically cytotoxic to human breast carcinoma cells overexpressing erbB-2" *Gene Therapy* 4(4):317-322 (Apr. 1997).

Wu et al., "Apoptosis Induced By an Anti-Epidermal Growth Factor Receptor Monoclonal Antibody in a Human Colorectal Carcinoma Cell Line and Its Delay by Insulin" *Journal of Clinical Investigation* 95(4):1897-1905 (Apr. 1995).

Xu et al., "Antibody-Induced Growth Inhibition is Mediated Through Immunochemically and Functionally Distinct Epitopes on the Extracellular Domain of the c-erbB-2 (HER-2/neu) Gene Product p185" *International Journal of Cancer* 53(3):401-408 (Feb. 1, 1993).

Yamamoto et al., "Similarity of protein encoded by the human c-erb-B-2 gene to epidermal growth factor receptor" *Nature* 319:230-234 (1986).

Yokota et al., "Amplification of c-erbB-2 Oncogene in Human Adenocarcinomas in Vivo" *Lancet* 1(8484):765-767 (Apr. 5, 1986).

Yonemura et al., "Evaluation of Immunoreactivity for erbB-2 Protein as a Marker of Poor Short Term Prognosis in Gastric Cancer" *Cancer Research* 51(3):1034-1038 (Feb. 1, 1991).

Zhang et al., "Relative malignant potential of human breast carcinoma cell lines established from pleural effusions and a brain metastasis" *Invasion Metastasis* 11(4):204-215 (1991).

Zhang et al., "Shared antigenic epitopes and pathobiological functions of anti-p185$^{her2/neu}$ monoclonal antibodies" *Experimental and Molecular Pathology* 67:15-25 (1999).

Zhau et al., "Amplification and Expression of the c-erb B-2/neu Proto-Oncogene in Human Bladder Cancer" *Molecular Carcinogenesis* 3(5):254-257 (1990).

Fahy et al., "Cellular and biochemical analysis of induced sputum from asthmatic and from healthy subjects" *Am. Rev. Respir. Dis.* 147:1126-1131 (1993).

Fick et al., "Bronchoalveolar Lavage in Allergic Asthmatics" *Am. Rev. Respir. Dis.* 135:1204-1209 (1987).

Fick et al., "Increased bronchovascular permeability after allergen exposure in sensitive asthmatics" *J. Appl. Physiol.* 63(3):1147-1155 (1987).

Fisher et al., "Biostatistics: a methodology for the health sciences", New York:John Wiley & Sons pp. 861-862 (1993).

Froehlich et al., "Multiple Doses of a Recombinant Humanized Monoclonal Anti IgE Antibody Are Safely Tolerated and Decrease Free Serum IgE to Undetectable Levels" *J. Allergy and Clinical Immunology* (Abstract #863) 95(1 Part II):356 (Jan. 1995).

Gamimune Package Insert.

Gammagard Package Insert.

Gammar Package Insert.

Geha et al., "IgE sites relevant for binding to type 1 Fc epsilon (FCER) recptor on mast cells" *J. Allergy & Clin. Immunol.* (Abstract No. 20) 79(1):129 (1987).

Gerber, D., "Copper-catalyzed thermal aggregation of human gamma-globulin. Inhibitio by histidine, gold thiomalate, and penicillamine" *Arthritis and Rheumatism* 17(1):85-91 (Jan.-Feb. 1974).

Grammer et al., "Diagnosis and classification of asthma" *Chest* 101(6):393S-395S (Jun. 1992).

Gundel et al., "Endothelial Leukocyte Adhesion Molecule-1 Mediates Antigen-Induced Acute Airway Inflammation and Late-Phase Airway Obstructin in Monkeys" *J. Clin. Invest.* 89:1407-1411 (Oct. 1991).

Hakimi et al., "The α subunit of the human IgE receptor (FcERI) is sufficient for high affinity IgE binding" *Journal of Biological Chemistry* 265(36):22079-22081 (1990).

Hargreave, F.E., "Late-phase asthmatic responses and airway inflammation" *J. Allergy Clin. Immunol.* 83(2):525-527 (Feb. 1989).

Helm et al., "Blocking of passive sensitization of human mast cells and basophil granulocytes with IgE antibodies by a recombinant human ε-chain fragment of 76 amino acids" *Proc. Natl. Acad. Sci.* 86:9465-9469 (Dec. 1989).

Helm et al., "The mast cell binding site on human immunoglobulin E" *Nature* 331:180-183 (Jan. 14, 1988).

Hoffman, D. R., "Enzyme-linked immunosorbent assays (ELISA) for immunoglobulin E and blocking antibodies" *Methods in Enzymology*, Chapter 45, 73:656-666 (1981).

Hook et al., "Monoclonal Antibodies Defining Epitopes on Human IgE" *Molecular Immunology* 28(6):631-639 (1991).

Hook et al., "Monoclonal antibodies defining epitopes on IgE" *Federation of American Societies for Experimental Biology* (71st Annual Meeting, Abstract #6008) pp. 1346 (1987).

Hook et al., "Monoclonal antibodies to human IgE" *Federation Proceedings* (Abstract No. 4177 Only) 40(3):968 (1994).

Hora et al., "Lyophilized formulations of recombinant tumor necrosis factor" *Pharmaceutical Research* 9(1):33-36 (Jan. 1992).

Hottiger et al., "The role of trehalose synthesis for the acquisition of thermotolerance in yeast. II. Physiological concentrations of trehalose increase the thermal stability of proteins in vitro" *European Journal of Biochemistry* 219(1-2):187-193 (Jan. 15, 1994).

Strobel and Cannistra, "β1-integrated partly mediate binding of ovarian cancer cells to peritoneal mesothelium in vitro" *Gynecologic Oncology* 73(3):362-367 (Jun. 1999).

Andya et al., "Mechanisms of aggregate formation and carbohydrate excipient stabilization of lyophilized humanized monoclonal antibody formulations" *AAPS PharmSci* (Article 10 (http://www.pharmsci.org)) 5(2):94-104 (2003).

Baniyash et al., "Anti-IgE monoclonal antibodies directed at the Fc$_\epsilon$receptor binding site" *Molecular Immunology* 25(8):705-711 (1988).

Baniyash et al., "Inhibition of IgE Binding to Mast Cells and Basophils by Monoclonal Antibodies to Murine IgE" *European Journal of Immunology* 14:799-807 (1984).

Berglund et al., "Spirometric studies in normal subjects" *Acta. Med. Scand.* 173:185-192 (1963).

Blank et al., "Characterization of Truncated α Chain Products from Human, Rat, and Mouse High Affinity Receptor for Immunoglobulin E" *Journal of Biological Chemistry* 266(4):2639-2646 (Feb. 5, 1991).

Boulianne et al., "Production of functional chimaeric mouse/human antibody" *Nature* 312:643-646 (Dec. 13, 1984).

Bozelka et al., "Effects of Anti-ε on Total and Specific IgE Levels in Adult Mice" *Int. Archs. Allergy Appl. Immun.* 78:51-56 (1985).

Bozelka et al., "IgE isotype suppression in anti-ε-treated mice" *Immunology* 46:527-532 (1982).

Burrows et al., "Association of asthma with serum IgE levels and skin-test reactivity to allergens" *New England J. of Medicine* 320(5):271-277 (Feb. 2, 1989).

Burt et al., "Analysis of the interaction between rat immunoglobulin E and rat mast cells using anti-peptide antibodies" *Molecular Immunology* 24(4):379-389 (1987).

Burt et al., "Inhibition of binding of rat IgE to rat mast cells by synthetic IgE peptiedes" *European Journal of Immunology* 17:437-440 (1987).

Carpenter et al., "Separation of freezing- and drying-induced denaturation of lyophilized proteins using stress-specific stabilization. I. Enzyme activity and calorimetric studies" *Archives of Biochemistry & Biophysics* 303(2):456-464 (Jun. 1993).

Chang et al., "Monoclonal Antibodies Specific for Human IgE-producing B Cells: A Potential Therapeutic for IgE-mediated Allergic Diseases" *Bio/Technology* 8:122-126 (Feb. 1990).

Cleland et al., "A specific molar ratio of stabilizer to protein is required for storage stability of a lyophilized monoclonal antibody" *Journal of Pharmaceutical Sciences* 90(3):310-321 (Mar. 2001).

Cockcroft et al., "Allergen-induced increase in non-allergic bronchial reactivity" *Clinical Allergy* 7:503-513 (1977).

Cockcroft et al., "Comparative effects of inhaled salbutamol, sodium cromoglycate, and beclomethasone dipropionate on allergen-induced early asthmatic responses, late asthmatic responses, and increased bronchial responsiveness to histamine" *J. Allergy Clin. Immunol.* 79(5):734-740 (May 1987).

Cockcroft et al., "Prediction of airway responsiveness to allergen from skin sensitivity to allergen and airway responsiveness to histamine" *Am. Rev. Respir. Dis.* 135:264-267 (1987).

Cockcroft et al., "rhuMAb-E25 (E25), Humanized Murine Monoclonal Anti-IgE, Inhibits the Allergen-induced Early Asthmatic Response (EAR)" *J. of Allergy and Clinical Immunology* (Abstract No. 532) 97(1 Part III):315 (Jan. 1996).

Cohn et al., "Induction of Airway Mucus Production By T Helper 2 (Th2) Cells: A Critical Role for Interleukin 4 in Cell Recruitment But Not Mucus Production" *Journal of Experimental Medicine* 186(10):1737-1747 (Nov. 17, 1997).

Conrad et al., "The Interaction of Human and Rodent IgE with the Human Basophil IgE Receptor" *J. of Immunology* 130(1):327-333 (1983).

Conrad, D.H., "FcεRII/CD23: The low affinity receptor for IgE" *Ann. Rev. Immunol.* 8:623-639 (1990).

Corrigan et al., "T Cells and Eosinophils in the Pathogenesis of Asthma" *Immunology Today* 13(12):501-507 (1992).

Coyle et al., "Central Role of Immunoglobulin (Ig) E in the Induction of Lung Eosinophil Infiltration and T Helper 2 Cell Cytokine Production: Inhibition by a Non-anaphylactogenic Anti-IgE Antibody" *Journal of Experimental Medicine* 183:1303-1310 (Apr. 1996).

Crescioli et al., "Theophylline inhibits early and late asthmatic reactions induced by allergens in asthmatic subjects" *Ann. Allergy* 66:245-251 (Mar. 1991).

Davis et al., "Can anti-IgE be used to treat allergy?" *Springer Seminars in Immunopathology* 15(1):51-73 (1993).

Diaz et al., "Leukocytes and mediators in bronchoalveolar lavage during allergen-induced late-phase asthmatic reactions" *Am. Rev. Respir. Dis.* 139:1383-1389 (1989).

Dodge et al., "The prevalence and incidence of asthma and asthma-like symptoms in a general population sample" *Am. Rev. Respir. Dis.* 122:567-575 (1980).

Fahy et al., "Analysis of cellular and biochemical constituents of induced sputum after allergen challenge: A method for studying allergic airway inflammation" *J. Allergy Clin. Immunol.* 93(6):1031-1039 (Jun. 1994).

Ishizaka, K., "Immunoglobulin E (IgE)" *Methods in Enzymology* 116 (Part II):76-94 (1985).

Kay et al., "Mediators of Hypersensitivity and Inflammatory Cells in Early- and Late-Phase Asthmatic Reactions" *Asthma: Physiology, Immunopharmacology and Treatment (3rd Int'l Symposium)* (Chp. 13), Kay et al., New York:Academic Press pp. 211-227 (1984).

Korsgren et al., "Allergic Eosinophil-rich Inflammation Develops in Lungs and Airways of B Cell-deficient Mice" *Journal of Experimental Medicine* 185(5):885-892 (Mar. 1997).

Kulczycki et al., "The Interaction of IgE with Rat Basophilic Leukemia Cells, Evidence for Specific Binding of IgE" *Journal of Experimental Medicine* 139:600-616 (1974).

Kurokawa et al., "Expression of human immunoglobulin E $\epsilon$ chain cDNA in *E. coli*" *Nucleic Acids Research* 11(10):3077-3085 (1983).

Larsen et al., "An Animal Model of the Late Asthmatic Response to Antigen Challenge" *Asthma: Physiology, Immunopharmacology and Treatment (3rd Int'l Symposium)* (Chp. 15), Kay et al., New York:Academic Press pp. 245-262 (1984).

Lazar et al., "Transforming Growth Factor $\alpha$: Mutation of Aspartic Acid 47 and Leucine 48 Results in Different Biological Activities" *Molecular & Cellular Biology* 8(3):1247-1252 (Mar. 1988).

Liu et al., "Expression of a biologically active fragment of human IgE $\epsilon$ chain in *Escherichia coli*" *Proc. Natl. Acad. Sci.* 81:5369-5373 (Sep. 1984).

Marsh et al., "Increases in Airway Reactivity to Histamine and Inflammatory Cells in Bronchoalveolar Lavage after the Late Asthmatic Response in an Animal Model" *Am. Rev. Respir. Dis.* 131:875-879 (1985).

Murray et al., "Dust-Free Bedrooms in the Treatment of Asthmatic Children with House Dust or House Dust Mite Allergy: A Controlled Trial" *Pediatrics* 71(3):418-422 (Mar. 1983).

Nakajima et al., "$CD4_+$T-Lymphocytes and Interleukin-5 Mediate Antigen-induced Eosinophil Infiltration into the Mouse Trachea" *Am. Rev. Respir. Dis.* 146:374-377 (1992).

Nakajima et al., "Effect of Saiboku-to (TJ-96) on Bronchial Asthma" *Annals of the New York Academy of Sciences* 685:549-560 (Jun. 23, 1993).

Neuberger et al., "A hapten-specific chimaeric IgE antibody with human physiological effector function" *Nature* 314:268-270 (Mar. 21, 1985).

Nio et al., "Inhibition of histamine release by synthetic human IgE peptide fragments: structure-activity studies" *Peptide Chemistry* pp. 203-208 (1989).

Nissim et al., "Mapping of the high affinity Fc$\epsilon$ receptor binding side to the third constant region domain of IgE" *EMBO Journal* 10(1):101-107 (Jan. 1991).

Platts-Mills et al., "Reduction of Bronchial Hyperreactivity During Prolonged Allergen Avoidance" *Lancet* 2(8300):675-678 (Sep. 25, 1982).

Prestrelski et al., "Separation of freezing- and drying-induced denaturation of lyophilized proteins using stress-specific stabilization. II. Structural studies using infrared spectroscopy" *Archives of Biochemistry & Biophysics* 303(2):465-473 (Jun. 1993).

Roberts et al., "An integrated strategy for structural characterization of the protein and carbohydrate components of monoclonal antibodies: application to anti-respiratory syncytial virus MAb" *Analytical Chemistry* 67(20):3613-3625 (Oct. 15, 1995).

Robertson et al., "IgE structure-function relationships defined by sequence directed antibodies induced by synthetic peptides" *Molecular Immunology* 25(2):103-113 (1988).

Rup et al., "Identification of a Mouse Anti-Rat IgE Monoclonal Antibody, 44.7b, Which Inhibits IgE Binding to RBL Cells" *International Archives of Allergy & Applied Immunology* 89(4):387-393 (1989).

Saban et al., "Human FcERI-IgG and Humanized Anti-IgE Monoclonal Antibody MaEll Block Passive Sensitization of Human and Rhesus Monkey Lung" *J. Allergy and Clinical Immunology* 94(5):836-843 (Nov. 1994).

Schwarzbaum et al., "Mapping of murine IgE epitopes involved in IgE-Fc$\epsilon$ receptor interactions" *European Journal of Immunology* 19:1015-1023 (1989).

Shields et al., "Inhibition of Allergic Reactions with Antibodies to IgE" *Inernational Archives of Allergy and Immunology* 107(1-3):308-312 (May 1995).

"Standardization of Spirometry—1987 Update" *Am. Rev. Respir. Dis.* (American Thoracic Society, Medical Section of the American Lung Association) 136:1285-1298 (1987).

Stanworth et al., "Synthetic peptides comprising sequences of the human immunoglobulin E heavy chain capable of releasing histamine" *Biochemical Journal* 180(3):665-668 (1979).

Takeda et al., "Development of Eosinophilic Airway Inflammation and Airway Hyperresponsiveness in Mast Cell-deficient Mice" *Journal of Experimental Medicine* 186(3):449-454 (Aug. 1997).

Tepper et al., "The Role of Mast Cells and IgE in Murine Asthma" *Asthma Theory to Treatment* (Abstract Only) pp. 8 (Jul. 15, 1995).

Townsend and DeLuca, "Nature of aggregates formed during storage of freeze-dried ribonuclease A" *Journal of Pharmaceutical Sciences* 80(1):63-66 (Jan. 1991).

Townsend and DeLuca, "Use of lyoprotectants in the freeze-drying of a model protein, ribonuclease A" *Journal of Parenteral Science & Technology* 42(6):190-199 (Nov.-Dec. 1988).

Tung, A. S., "Production, purification, and characterization of antigen-specific murine monoclonal antibodies of IgE class" *Methods in Enzymology*, Chapter 6, 92:47-66 (1983).

Vercelli et al., "The B-cell binding site on human immunoglobulin E" *Nature* 338:649-651 (Apr. 20, 1989).

Ward et al., "Theophylline—an Immunomodulatory Role in Asthma?" *Am. Rev. Respir. Dis.* 147(3):518-523 (1993).

Weetall et al., "Mapping the site of interaction between murine IgE and its high affinity receptor with chimeric Ig" *J. Immunol.* 145(11):3849-3854 (Dec. 1, 1990).

Weiss et al., "The Interrelationship Among Allergy, Airways Responsiveness, and Asthma" *J. Asthma* 30(5):329-349 (1993).

Zweiman, B., "The Late-Phase Reaction: Role of IgE, Its Receptor and Cytokines" *Current Opinion in Immunology* 5:950-955 (1993).

US 5,036,049, 07/1991, Audhya et al. (withdrawn)

PROTEIN FORMULATION

This is a continuation of divisional application Ser. No. 09/273,230 filed Mar. 18, 1999, now abandoned which claims priority to application Ser. No. 08/615,369 filed Mar. 14, 1996 (now U.S. Pat. No. 6,267,958 B1), which is a non-provisional filed under 37 CFR 1.53(b) claiming priority under 35 USC 119(e) to provisional application Ser. No. 60/029,182 filed Jul. 27, 1995, now abandoned the contents of which are incorporated herein by reference.

BACKGROUND OF THE INVENTION

1. Field of the Invention

This invention is directed to a lyophilized protein formulation. In particular, it relates to a stable lyophilized protein formulation which can be reconstituted with a diluent to generate a stable reconstituted formulation suitable for subcutaneous administration.

2. Description of Related Disclosures

In the past ten years, advances in biotechnology have made it possible to produce a variety of proteins for pharmaceutical applications using recombinant DNA techniques. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al. *Critical Reviews in Therapeutic Drug Carrier Systems* 10(4): 307-377 (1993).

Freeze-drying is a commonly employed technique for preserving proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. *Biopharm.* 3(9)26-30 (1990) and Arakawa et al. *Pharm. Res.* 8(3):285-291 (1991).

It is an object of the present invention to provide a lyophilized protein formulation which is stable upon storage and delivery. It is a further object to provide a stable reconstituted protein formulation which is suitable for subcutaneous administration. In certain embodiments, it is an object to provide a multi-use formulation which is stable for at least the time over which it will be administered to a patient.

SUMMARY OF THE INVENTION

This invention is based on the discovery that a stable lyophilized protein formulation can be prepared using a lyoprotectant (preferably a sugar such as sucrose or trehalose), which lyophilized formulation can be reconstituted to generate a stable reconstituted formulation having a protein concentration which is significantly higher (e.g. from about 2-40 times higher, preferably 3-10 times higher and most preferably 3-6 times higher) than the protein concentration in the pre-lyophilized formulation. In particular, while the protein concentration in the pre-lyophilized formulation may be 5 mg/mL or less, the protein concentration in the reconstituted formulation is generally 50 mg/mL or more. Such high protein concentrations in the reconstituted formulation are considered to be particularly useful where the formulation is intended for subcutaneous administration. Despite the very high protein concentration in the reconstituted formulation, it has been found that the reconstituted formulation is stable (i.e. fails to display significant or unacceptable levels of chemical or physical instability of the protein) at 2-8° C. for at least about 30 days. In certain embodiments, the reconstituted formulation is isotonic. In spite of the use of lower concentrations of the lyoprotectant to achieve such isotonic formulations upon reconstitution, it was discovered herein that the protein in the lyophilized formulation essentially retains its physical and chemical stability and integrity upon lyophilization and storage.

When reconstituted with a diluent comprising a preservative (such as bacteriostatic water for injection, BWFI), the reconstituted formulation may be used as a multi-use formulation. Such a formulation is useful, for example, where the patient requires frequent subcutaneous administrations of the protein to treat a chronic medical condition. The advantage of a multi-use formulation is that it facilitates ease of use for the patient, reduces waste by allowing complete use of vial contents, and results in a significant cost savings for the manufacturer since several doses are packaged in a single vial (lower filling and shipping costs).

Based on the observations described herein, in one aspect the invention provides a stable isotonic reconstituted formulation comprising a protein in an amount of at least about 50 mg/mL and a diluent, which reconstituted formulation has been prepared from a lyophilized mixture of a protein and a lyoprotectant, wherein the protein concentration in the reconstituted formulation is about 240 times greater than the protein concentration in the mixture before lyophilization.

In another embodiment, the invention provides a stable reconstituted formulation comprising an antibody in an amount of at least about 50 mg/mL and a diluent, which reconstituted formulation has been prepared from a lyophilized mixture of an antibody and a lyoprotectant, wherein the antibody concentration in the reconstituted formulation is about 2-40 times greater than the antibody concentration in the mixture before lyophilization.

The ratio of lyoprotectant:protein in the lyophilized formulation of the preceding paragraphs depends, for example, on both the protein and lyoprotectant of choice, as well as the desired protein concentration and isotonicity of the reconstituted formulation. In the case of a full length antibody (as the protein) and trehalose or sucrose (as the lyoprotectant) for generating a high protein concentration isotonic reconstituted formulation, the ratio may, for example, be about 100-1500 mole trehalose or sucrose:1 mole antibody.

Generally, the pre-lyophilized formulation of the protein and lyoprotectant will further include a buffer which provides the formulation at a suitable pH, depending on the protein in the formulation. For this purpose, it has been found to be desirable to use a histidine buffer in that, as demonstrated below, this appears to have lyoprotective properties.

The formulation may further include a surfactant (e.g. a polysorbate) in that it has been observed herein that this can reduce aggregation of the reconstituted protein and/or reduce the formation of particulates in the reconstituted formulation. The surfactant can be added to the pre-lyophilized formulation, the lyophilized formulation and/or the reconstituted formulation (but preferably the pre-lyophilized formulation) as desired.

The invention further provides a method for preparing a stable isotonic reconstituted formulation comprising reconstituting a lyophilized mixture of a protein and a lyoprotectant in a diluent such that the protein concentration in the reconstituted formulation is at least 50 mg/mL, wherein the protein concentration in the reconstituted formulation is about 2-40 times greater than the protein concentration in the mixture before lyophilization.

In yet a further embodiment, the invention provides a method for preparing a formulation comprising the steps of: (a) lyophilizing a mixture of a protein and a lyoprotectant; and (b) reconstituting the lyophilized mixture of step (a) in a diluent such that the reconstituted formulation is isotonic and stable and has a protein concentration of at least about 50 mg/mL. For example, the protein concentration in the reconstituted formulation may be from about 80 mg/mL to about 300 mg/mL. Generally, the protein concentration in the reconstituted formulation is about 240 times greater than the protein concentration in the mixture before lyophilization.

An article of manufacture is also provided herein which comprises: (a) a container which holds a lyophilized mixture of a protein and a lyoprotectant; and (b) instructions for reconstituting the lyophilized mixture with a diluent to a protein concentration in the reconstituted formulation of at least about 50 mg/mL. The article of manufacture may further comprise a second container which holds a diluent (e.g. bacteriostatic water for injection (BWFI) comprising an aromatic alcohol).

The invention further provides a method for treating a mammal comprising administering a therapeutically effective amount of a reconstituted formulation disclosed herein to a mammal, wherein the mammal has a disorder requiring treatment with the protein in the formulation. For example, the formulation may be administered subcutaneously.

One useful anti-HER2 antibody pre-lyophilized formulation as discovered in the experiments detailed below was found to comprise anti-HER2 in amount from about 5-40 mg/mL (e.g. 20-30 mg/mL) and sucrose or trehalose in an amount from about 10-100 mM (e.g. 40-80 mM), a buffer (e.g. histidine, pH 6 or succinate, pH 5) and a surfactant (e.g. a polysorbate). The lyophilized formulation was found to be stable at 40° C. for at least 3 months and stable at 30° C. for at least 6 months. This anti-HER2 formulation can be reconstituted with a diluent to generate a formulation suitable for intravenous administration comprising anti-HER2 in an amount from about 10-30 mg/mL which is stable at 2-8° C. for at least about 30 days. Where higher concentrations of the anti-HER2 antibody are desired (for example where subcutaneous delivery of the antibody is the intended mode of administration to the patient), the lyophilized formulation may be reconstituted to yield a stable reconstituted formulation having a protein concentration of 50 mg/mL or more.

One desirable anti-IgE antibody pre-lyophilized formulation discovered herein has anti-IgE in amount from about 5-40 mg/mL (e.g. 20-30 mg/mL) and sucrose or trehalose in an amount from about 60-300 mM (e.g. 80-170 mM), a buffer (preferably histidine, pH 6) and a surfactant (such as a polysorbate). The lyophilized anti-IgE formulation is stable at 30° C. for at least 1 year. This formulation can be reconstituted to yield a formulation comprising anti-IgE in an amount from about 15-45 mg/mL (e.g. 15-25 mg/mL) suitable for intravenous administration which is stable at 2-8° C. for at least 1 year. Alternatively, where higher concentrations of anti-IgE in the formulation are desired, the lyophilized formulation can be reconstituted in order to generate a stable formulation having an anti-IgE concentration of $\geq$50 mg/mL.

TABLE 1

| Moles of Sugar: E25 antibody | Sugar conc. (mM) |
|---|---|
| 0 | 0 |
| 260 | 34.4 |
| 380 | 51.6 |
| 510 | 68.8 |
| 760 | 103.1 |
| 1020 | 137.5 |
| 1530 | 206.3 |
| 2010 | 275 |

Figure 17:
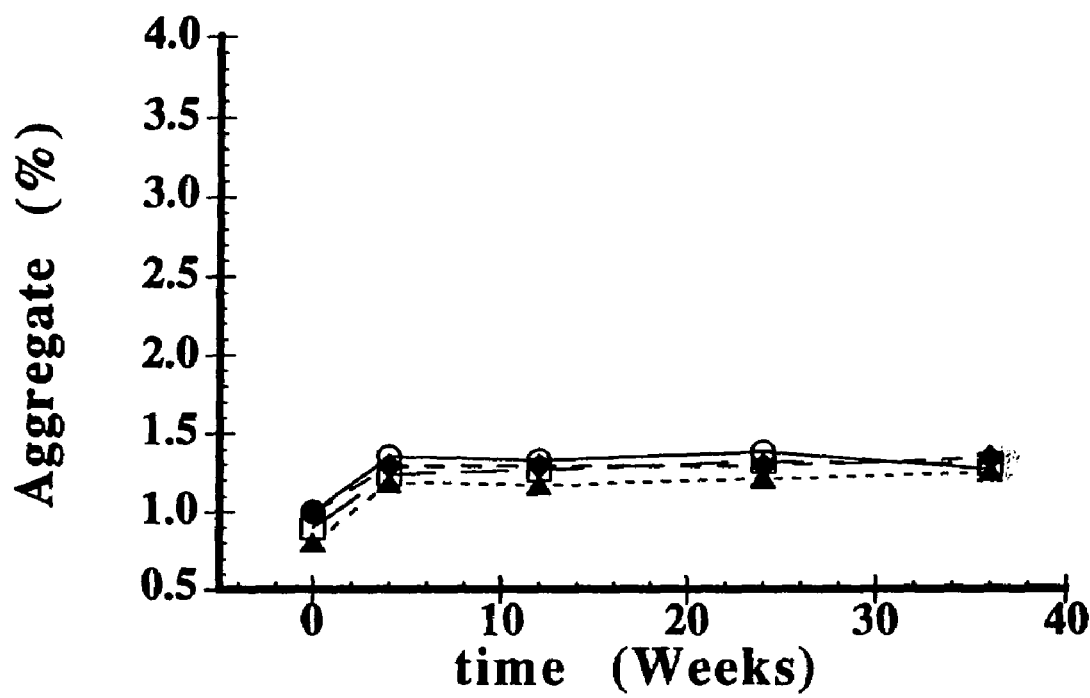

FIG. 17 reveals aggregation of rhuMAb E25 formulated at 25 mg/mL into 5 mM histidine at pH 6 with 85 mM sucrose (○); 85 mM trehalose (□); 161 mM sucrose (◆) or 161 mM trehalose (▲). Samples were lyophilized and stored at 2-8° C. followed by reconstitution with 0.9% benzyl alcohol to 100 mg/mL antibody in 20 mM histidine at pH 6 with isotonic (340 mM) and hypertonic (644 mM) sugar concentration.

Figure 18:
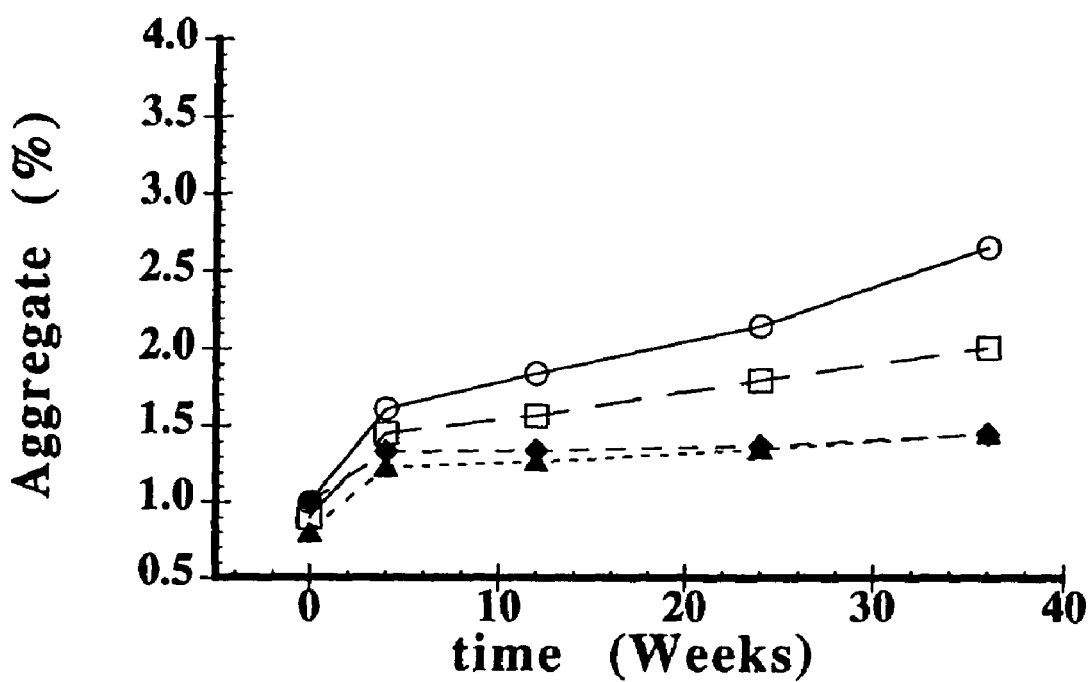

FIG. 18 shows aggregation of rhuMAb E25 formulated at 25 mg/mL into 5 mM histidine at pH 6 with 85 mM sucrose (○); 85 mM trehalose (□); 161 mM sucrose (◆) or 161 mM trehalose (▲). Samples were lyophilized and stored at 30° C. followed by reconstitution with 0.9% benzyl alcohol to 100 mg/mL antibody in 20 mM histidine at pH 6 with isotonic (340 mM) and hypertonic (644 mM) sugar concentration.

Figure 19:
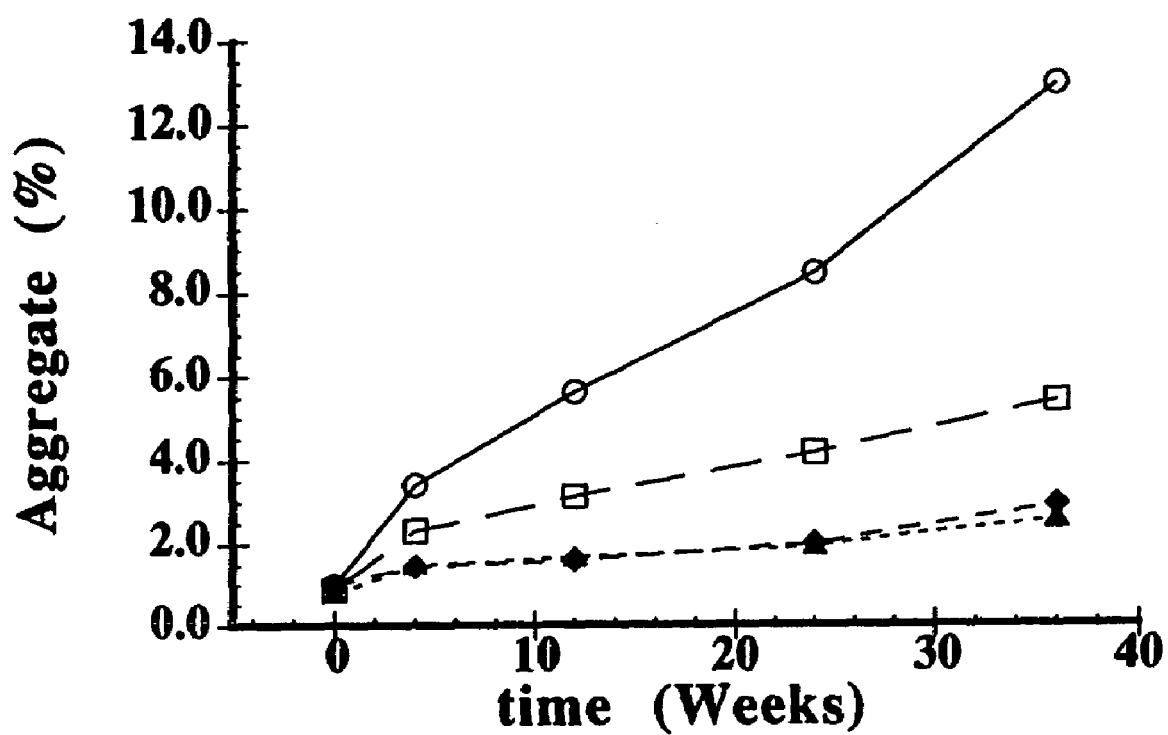

FIG. 19 illustrates aggregation of rhuMAb E25 formulated at 25 mg/mL into 5 mM histidine at pH 6 with 85 mM sucrose (○); 85 mM trehalose (□); 161 mM sucrose (◆) or 161 mM trehalose (▲). Samples were lyophilized and stored at 50° C. followed by reconstitution with 0.9% benzyl alcohol to 100 mg/mL antibody in 20 mM histidine at pH 6 with isotonic (340 mM) and hypertonic (644 mM) sugar concentration.

DETAILED DESCRIPTION OF THE PREFERRED EMBODIMENTS

I. Definitions

By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

Examples of proteins encompassed within the definition herein include mammalian proteins, such as, e.g., growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

The protein which is formulated is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

In certain embodiments, the protein is an antibody. The antibody may bind to any of the above-mentioned molecules, for example. Exemplary molecular targets for antibodies encompassed by the present invention include CD proteins such as CD3, CD4, CD8, CD 19, CD20 and CD34; members of the HER receptor family such as the EGF receptor, HER2, HER3 or HER4 receptor; cell adhesion molecules such as LFA-1, Mol, p150, 95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; protein C etc.

The term "antibody" is used in the broadest sense and specifically covers monoclonal antibodies (including full length antibodies which have an immunoglobulin Fc region), antibody compositions with polyepitopic specificity, bispecific antibodies, diabodies, and single-chain molecules, as well as antibody fragments (e.g., Fab, F(ab')$_2$, and Fv).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321:522-525 (1986); Reichmann et al., *Nature,* 332:323-329 (1988); and Presta, *Curr. Op. Struct. Biol.,* 2:593-596 (1992). The humanized antibody includes a Primatized™ antibody wherein the antigen-binding region of the antibody is derived from an antibody produced by immunizing macaque monkeys with the antigen of interest.

A "stable" formulation is one in which the protein therein essentially retains its physical and chemical stability and integrity upon storage. Various analytical techniques for measuring protein stability are available in the art and are reviewed in *Peptide and Protein Drug Delivery,* 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30°

C., generally the formulation should be stable for at least 2 years at 30° C. and/or stable at 40° C. for at least 6 months. For example, the extent of aggregation following lyophilization and storage can be used as an indicator of protein stability (see Examples herein). For example, a "stable" formulation may be one wherein less than about 10% and preferably less than about 5% of the protein is present as an aggregate in the formulation. In other embodiments, any increase in aggregate formation following lyophilization and storage of the lyophilized formulation can be determined. For example, a "stable" lyophilized formulation may be one wherein the increase in aggregate in the lyophilized formulation is less than about 5% and preferably less than about 3%, when the lyophilized formulation is stored at 2-8° C. for at least one year. In other embodiments, stability of the protein formulation may be measured using a biological activity assay (see, e.g., Example 2 below).

A "reconstituted" formulation is one which has been prepared by dissolving a lyophilized protein formulation in a diluent such that the protein is dispersed in the reconstituted formulation. The reconstituted formulation in suitable for administration (e.g. parenteral administration) to a patient to be treated with the protein of interest and, in certain embodiments of the invention, may be one which is suitable for subcutaneous administration.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "lyoprotectant" is a molecule which, when combined with a protein of interest, significantly prevents or reduces chemical and/or physical instability of the protein upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. The preferred lyoprotectant is a non-reducing sugar, such as trehalose or sucrose.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

The "diluent" of interest herein is one which is pharmaceutically acceptable (safe and non-toxic for administration to a human) and is useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

A "preservative" is a compound which can be added to the diluent to essentially reduce bacterial action in the reconstituted formulation, thus facilitating the production of a multi-use reconstituted formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "bulking agent" is a compound which adds mass to the lyophilized mixture and contributes to the physical structure of the lyophilized cake (e.g. facilitates the production of an essentially uniform lyophilized cake which maintains an open pore structure). Exemplary bulking agents include mannitol, glycine, polyethylene glycol and xorbitol.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the protein. This includes chronic and acute disorders or diseases including those pathological conditions which predispose the mammal to the disorder in question. Non-limiting examples of disorders to be treated herein include carcinomas and allergies.

II. Modes for Carrying out the Invention

A. Protein Preparation

The protein to be formulated is prepared using techniques which are well established in the art including synthetic techniques (such as recombinant techniques and peptide synthesis or a combination of these techniques) or may be isolated from an endogenous source of the protein. In certain embodiments of the invention, the protein of choice is an antibody. Techniques for the production of antibodies follow.

(i) Polyclonal Antibodies.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining 1 mg or 1 μg of the peptide or conjugate (for rabbits or mice, respectively) with 3 volumes of Freund's complete adjuvant. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495(1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iii) Humanized and Human Antibodies.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993). Human antibodies can also be derived from phage-display libraries (Hoogenboom et al., *J. Mol. Biol.*, 227:381 (1991); Marks et al., *J. Mol. Biol.*, 222:581-597 (1991)).

(iv) Bispecific Antibodies

Bispecific antibodies (BsAbs) are antibodies that have binding specificities for at least two different epitopes. Such antibodies can be derived from full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. For example, Fab' fragments recovered from *E. coli* can be chemically coupled in vitro to form bivalent antibodies. See, Shalaby et al., *J. Exp. Med.*, 175:217-225 (1992).

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA*, 90:6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

B. Preparation of the Lyophilized Formulation

After preparation of the protein of interest as described above, a "pre-lyophilized formulation" is produced. The amount of protein present in the pre-lyophilized formulation is determined taking into account the desired dose volumes, mode(s) of administration etc. Where the protein of choice is an intact antibody (such as an anti-IgE or anti-HER2 antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in *Remington's Pharmaceutical Sciences* 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulation herein may also contain more than one protein as necessary for the particular indication being treated, preferably those with complementary activities that do not adversely affect the other protein. For example, it may be desirable to provide two or more antibodies which bind to the HER2 receptor or IgE in a single formulation. Furthermore, anti-HER2 and anti-VEGF antibodies may be combined in the one formulation. Such proteins are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

As a general proposition, lyophilization will result in a lyophilized formulation in which the moisture content thereof is less than about 5%, and preferably less than about 3%.

C. Reconstitution of the Lyophilized Formulation

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Preferably, the reconstituted formulation has less than 6000 particles per vial which are $\geqq 10$ μm in size.

D. Administration of the Reconstituted Formulation

The reconstituted formulation is administered to a mammal in need of treatment with the protein, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the reconstituted formulation is administered to the mammal by subcutaneous (i.e. beneath the skin) administration. For such purposes, the formulation may be injected using a syringe. However, other devices for administration of the formulation are available such as injection devices (e.g. the Inject-ease™ and Genject™ devices); injector pens (such as the GenPen™); needleless devices (e.g. MediJector™ and BioJector™); and subcutaneous patch delivery systems.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question.

Where the protein of choice is an antibody, from about 0.1-20 mg/kg is an initial candidate dosage for administration to the patient, whether, for example, by one or more separate administrations. However, other dosage regimens may be useful. The progress of this therapy is easily monitored by conventional techniques.

In the case of an anti-HER2 antibody, a therapeutically effective amount of the antibody may be administered to treat or prevent cancer characterized by overexpression of the HER2 receptor. It is contemplated that a reconstituted formulation of the anti-HER2 antibody may be used to treat breast, ovarian, stomach, endometrial, salivary gland, lung, kidney, colon and/or bladder cancer. For example, the anti-HER2 antibody may be used to treat ductal carcinoma in situ (DCIS). Exemplary dosages of the anti-HER2 antibody are in the range 1-10 mg/kg by one or more separate administrations.

Uses for an anti-IgE formulation include the treatment or prophylaxis of IgE-mediated allergic diseases, parasitic infections, interstitial cystitis and asthma, for example. Depending on the disease or disorder to be treated, a therapeutically effective amount (e.g. from about 1-15 mg/kg) of the anti-IgE antibody is administered to the patient.

E. Articles of Manufacture

In another embodiment of the invention, an article of manufacture is provided which contains the lyophilized formulation of the present invention and provides instructions for its reconstitution and/or use. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the lyophilized formulation and the label on, or associated with, the container may indicate directions for reconstitution and/or use. For example, the label may indicate that the lyophilized formulation is reconstituted to protein concentrations as described above. The label may further indicate that the formulation is useful or intended for subcutaneous administration. The container holding the formulation may be a multi-use vial, which allows for repeat administrations (e.g. from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All literature citations are incorporated by reference.

Example 1

Anti-HER2 Formulation

Overexpression of the HER2 proto-oncogene product (p185$^{HER2}$) has been associated with a variety of aggressive human malignancies. The murine monoclonal antibody known as muMAb4D5 is directed against the extracellular domain (ECD) of p185$^{HER2}$. The muMAb4D5 molecule has been humanized in an attempt to improve its clinical efficacy by reducing immunogenicity and allowing it to support human effector functions (see WO 92/22653). This example describes the development of a lyophilized formulation comprising full length humanized antibody huMAb4D5-8 described in WO 92/22653.

In the development of a lyophilized formulation, excipients and buffers are initially screened by measuring the stability of the protein after lyophilization and reconstitution. The lyophilized protein in each formulation is also subjected to accelerated stability studies to determine the potential stability of the protein over its shelf-life. These accelerated studies are usually performed at temperatures above the proposed storage conditions and the data are then used to estimate the activation energy for the degradation reactions assuming Arrhenius kinetics (Cleland et al., *Critical Reviews in Therapeutic Drug Carrier Systems* 10(4): 307-377 (1993)). The activation energy is then used to calculate the expected shelf-life of the protein formulation at the proposed storage conditions.

In early screening studies, the stability of several lyophilized recombinant humanized anti-HER2 antibody (rhuMAb HER2) formulations was investigated after incubation at 5° C. (proposed storage condition) and 40° C. (accelerated stability condition). In the liquid state, rhuMAb HER2 was observed to degrade by deamidation (30 Asn of light chain) and isoaspartate formation via a cyclic imide intermediate, succinimide (102 Asp of heavy chain). The deamidation was minimized at pH 5.0 resulting in degradation primarily at the succinimide. At pH 6.0, slightly greater deamidation was observed in the liquid protein formulation. The lyophilized formulations were therefore studied with: (a) 5 or 10 mM succinate buffer, pH 5.0 or (b) 5 or 10 mM histidine buffer, pH 6.0. Both buffers contained the surfactant, polysorbate 20 (Tween 20™), which was employed to reduce the potential for aggregation of the reconstituted protein and minimize the formation of particulates after reconstitution. These buffers were used with and without various sugars. The protein was formulated in the buffer at 5.0, 21.0 or 25.0 mg/mL. These formulations were then lyophilized and assessed for protein stability after 2 weeks at 5° C. and 40° C. In the lyophilizer, the vials were frozen at a shelf temperature of −55° C. for approximately 5 hours followed by primary drying at a shelf temperature of 5° C. and 150 mTorr for 30 hours, and drying to 1-2% residual moisture was achieved with secondary drying at a shelf temperature of 20° C. for 10 hours. The major degradation route for this protein upon lyophilization was aggregation, and therefore the protein stability was assessed by native size exclusion chromatography to measure the recovery of intact native protein (% intact protein in Table 2 below).

The stabilizing effects of various lyoprotectant sugars on lyophilized protein was measured in 10 mM sodium succinate, pH 5.0 (Table 2). At high sugar concentrations (250-275 mM) and low protein concentration (5.0 mg/mL), trehalose and lactose stabilized the protein against aggregation for the lyophilized protein stored for 2 weeks at 40° C. However, lactose, a reducing sugar, was observed to react with the protein over longer term storage at 40° C. The formulations at 5.0 mg/mL protein containing either sorbitol or mannitol yielded aggregated protein after storage at 40° C. for 2 weeks. At the higher protein concentration (21.0 mg/mL), formulations comprising mannitol, or mannitol in combination with sorbitol or glycine, contained aggregated protein after lyophilization and storage at both conditions. In contrast, trehalose and sucrose prevented aggregation at both storage conditions.

The 250 mM trehalose and 250 mM lactose formulations were assessed for long term stability. After 9 months at 40° C. or 12 months at 5° C., there was no change in the % intact protein for the trehalose formulation. For the lactose formulation, the % intact protein remained constant (same as initial) after 3 months at 40° C. or 6 months at 25° C. The trehalose formulation could be stored at controlled room temperature (15-30° C.) for 2 years without a significant change in % intact protein.

The 10 mM histidine, pH 6.0 formulation with mannitol contained less aggregated protein after storage at 40° C. for 2 weeks than the 10 mM succinate formulation, pH 5.0 with mannitol. This result may be related to some stabilizing effect contributed by histidine alone. After storage at 40° C. for 2 weeks, there was, however, significant aggregation for histidine alone or histidine/mannitol formulations. The addition of sucrose at an equal mass to mannitol (10 mg/mL of each) in the histidine formulation stabilized the protein against aggregation for both storage conditions. The use of glycine with mannitol did not improve the protein stability, while the sucrose/glycine formulation provided the same stability as the sucrose/mannitol formulation. These results further indicated that sucrose was useful for preventing aggregation of the lyophilized protein during storage.

TABLE 2

| [Protein][b] (mg/mL) | Formulation | Liquid (5° C.) | Lyophilized (2 wk, 5° C.) | Lyophilized (2 wk, 40° C.) |
|---|---|---|---|---|
| | 10 mM sodium succinate pH 5.0 | | | |
| 5.0 | 275 mM trehalose, 0.01% Tween 20 ™ | 98.9 | 99.1 | 98.9 |
| 5.0 | 275 mM lactose, 0.01% Tween 20 ™ | 96.8 | 96.5 | 96.6 |
| 5.0 | 275 mM sorbitol, 0.01% Tween 20 ™ | 99.4 | 99.3 | 95.4 |
| 5.0 | 250 mM mannitol, 0.01% Tween 20 ™ | 100.0 | 99.9 | 98.8 |
| 5.0 | 250 mM trehalose, 0.01% Tween 20 ™ | 100.0 | 99.9 | 100.0 |
| 5.0 | 250 mM lactose, 0.01% Tween 20 ™ | 100.0 | 100.0 | 100.0 |
| 21.0 | 250 mM trehalose, 0.2% Tween 20 ™ | 99.3 | 99.1 | 99.1 |
| 21.0 | 250 mM sucrose, 0.2% Tween 20 ™ | 99.6 | 99.6 | 99.7 |
| 21.0 | 250 mM mannitol, 0.01% Tween 20 ™ | 100.0 | 94.6 | 94.0 |
| 21.0 | 188 mM mannitol/63 mM sorbitol, 0.01% Tween 20 ™ | 99.8 | 98.6 | 96.5 |
| 21.0 | 250 mM mannitol/25 mM glycine, 0.01% Tween 20 ™ | 99.5 | 96.5 | 96.4 |
| | 10 mM histidine pH 6.0 | | | |
| 21.0 | No sugar, 0.01% Tween 20 ™ | 100.0 | 99.9 | 98.9 |
| 21.0 | 54.9 mM mannitol, 0.01% Tween 20 ™ | 100.0 | 99.9 | 99.2 |
| 21.0 | 29.2 mM sucrose/266.4 mM glycine, 0.01% Tween 20 ™ | 100.0 | 100.0 | 99.6 |
| 21.0 | 54.9 mM mannitol/266.4 mM glycine, 0.01% Tween 20 ™ | 100.0 | 99.8 | 98.9 |
| 21.0 | 54.9 mM mannitol/29.2 mM sucrose, 0.01% Tween 20 ™ | 99.8 | 100.0 | 99.7 |

[a]The fraction of intact protein was measured by native size exclusion HPLC and the peak area of the native protein relative to the total peak area including aggregates (TSK3000 SW XL column, TosoHaas, with a flow rate of 1.0 mL/min; elution with phosphate buffered saline; detection at 214 and 280 nm). The protein formulations were analyzed before lyophilization (liquid, 5° C.) and after lyophilization and storage at 5° C. or 40° C. for 2 weeks.
[b]Formulations containing 5 mg/mL protein were reconstituted with distilled water (20 mL, 5.0 mg/mL protein), and formulations containing 21 mg/mL protein were reconstituted with bacteriostatic water for injection (BWFI, 0.9% benzyl alcohol; 20 mL, 20 mg/mL protein).

The delivery of a high protein concentration is often required for subcutaneous administration due to the volume limitations ($\leq 1.5$ mL) and dosing requirements ($\geq 100$ mg). However, high protein concentrations ($\geq 50$ mg/mL) are often difficult to achieve in the manufacturing process since at high concentrations, the protein has a tendency to aggregate during processing and becomes difficult to manipulate (e.g. pump) and sterile filter. Alternatively, the lyophilization process may provide a method to allow concentration of the protein. For example, the protein is filled into vials at a volume (Vf) and then lyophilized. The lyophilized protein is then reconstituted with a smaller volume (Vr) of water or preservative (e.g. BWFI) than the original volume (e.g. Vr=0.25Vf) resulting in a higher protein concentration in the reconstituted solution. This process also results in the concentration of the buffers and excipients. For subcutaneous administration, the solution is desirably isotonic.

The amount of trehalose in the lyophilized rhuMAb HER2 was reduced to produce an isotonic solution upon reconstitution to yield 100 mg/mL protein. The stabilizing effect of trehalose was determined as a function of concentration for 5 mM sodium succinate, pH 5.0 and 5 mM histidine, pH 6.0 at 25.0 mg/mL protein (Table 3). At trehalose concentrations from 60 to 200 mM, there was no significant aggregation after incubation of the lyophilized protein for 4 weeks at 40° C. These formulations were reconstituted with 20 mL of bacteriostatic water for injection (BWFI, USP, 0.9% benzyl alcohol). Reconstitution of the 50 mM trehalose formulation (5 mM sodium succinate) with 4 mL of BWFI (100 mg/mL protein) after incubation for 4 weeks at 40° C. yielded a slight increase in aggregate formation. The preserved reconstituted formulations provided the advantage of multiple withdrawals from the same vial without sterility concerns. When sterile needles are used, these formulations would then allow for several doses from a single vial.

TABLE 3

| [Protein] (mg/mL) | Formulation | Liquid (5° C.) | Lyophilized (4 wk, 5° C.) | Lyophilized (4 wk, 40° C.) |
|---|---|---|---|---|
| | 5 mM sodium succinate pH 5.0 | | | |
| 25.0 | 50 mM trehalose, 0.01% Tween 20 ™[b] | 100.00 | 100.0 | 99.5 |
| 25.0 | 60 mM trehalose, 0.01% Tween 20 ™ | 100.0 | 100.0 | 99.9 |
| 25.0 | 60 mM trehalose, 0.01% Tween 20 ™ | 100.0 | 100.0 | 99.2 |

TABLE 3-continued

| Composition Prior to Lyophilization | | % Intact Protein[a] | | |
|---|---|---|---|---|
| [Protein] (mg/mL) | Formulation | Liquid (5° C.) | Lyophilized (4 wk, 5° C.) | Lyophilized (4 wk, 40° C.) |
| 25.0 | 100 mM trehalose, 0.01% Tween 20 ™ | 100.0 | 100.0 | 99.7 |
| 25.0 | 150 mM trehalose, 0.01% Tween 20 ™ | 100.0 | 100.0 | 99.8 |
| 25.0 | 200 mM trehalose, 0.01% Tween 20 ™ 5 mM histidine pH 6.0 | 100.0 | 100.0 | 100.0 |
| 25.0 | 38.4 mM mannitol/20.4 mM sucrose, 0.01% Tween 20 ™ | 100.0 | 100.0 | 99.3 |
| 25.0 | 38.4 mM mannitol/20.4 mM sucrose, 0.01% Tween 20 ™[c] | 100.0 | 100.0 | 99.4 |
| 25.0 | 60 mM trehalose, 0.01% Tween 20 ™[d] | 100.0 | 100.0 | 99.8 |
| 25.0 | 60 mM trehalose, 0.01% Tween 20 ™ | 100.0 | 100.0 | 99.4 |
| 25.0 | 100 mM trehalose, 0.01% Tween 20 ™ | 100.0 | 100.0 | 99.6 |
| 25.0 | 150 mM trehalose, 0.01% Tween 20 ™ | 100.0 | 100.0 | 100.0 |
| 25.0 | 200 mM trehalose, 0.01% Tween 20 ™ | 100.0 | 100.0 | 100.0 |

[a]The fraction of intact protein was measured by native size exclusion HPLC and defined as the peak area of the native protein relative to the total peak area including aggregates (TSK3000 SW XL column, TosoHaas, with a flow rate of 1.0 mL/min; elution with phosphate buffered saline; detection at 214 and 280 nm). The protein formulations were analyzed before lyophilization (liquid, 5° C.) and after lyophilization and storage at 5° C. or 40° C. for 4 weeks. Formulations were reconstituted with bacteriostatic water for injection (BWFI, USP, 0.9% w/w benzyl alcohol; 20 mL, 22 mg/mL protein).
[b]Reconstituted with 4 mL of BWFI (0.9% benzyl alcohol) to yield 100 mg/mL protein.
[c]Reconstituted with 4 mL of BWFI (1.1% benzyl alcohol) to yield 100 mg/mL protein.
[d]Sample incubated for 2 weeks at 5° C. or 40° C. and then reconstituted with 20 mL of BWFI (0.9% benzyl alcohol) to yield 22 mg/mL protein.

Currently, rhuMAb HER2 is under investigation as a therapeutic for the treatment of breast cancer. The protein is dosed to patients at 2 mg/kg on a weekly basis. Since the average weight of these patients is 65 kg, the average weekly dose is 130 mg of rhuMAb HER2. For subcutaneous administration, injection volumes of 1.5 mL or less are well tolerated and, therefore, the protein concentration for a weekly subcutaneous administration of rhuMAb HER2 may be approximately 100 mg/mL (130 mg average dose/1.5 mL). As mentioned above, this high protein concentration is difficult to manufacture and maintain in a stable form. To achieve this high protein concentration, rhuMAb HER2 formulated in: (a) 5 mM sodium succinate, pH 5.0 or (b) 5 mM histidine, pH 6.0, was lyophilized at 25 mg/mL protein in 60 mM trehalose, 0.01% Tween 20™. The lyophilization was performed by filling 18 mL of the protein formulation into 50 cc vials. In the lyophilizer, the vials were frozen at a shelf temperature of −55° C. for approximately 5 hours followed by primary drying at a shelf temperature of 5° C. and 150 mTorr for 30 hours, and drying to 1-2% residual moisture was achieved with secondary drying at a shelf temperature of 20° C. for 10 hours. Thermocouples placed in vials containing the placebo (formulation without protein) indicated that the product in the vials was maintained below −10° C. throughout primary drying. Sequential stoppering studies during the lyophilization revealed that the residual moisture after primary drying was usually less than 10%.

The lyophilized protein was then reconstituted with either 4 or 20 mL of BWFI (0.9 or 1.1% benzyl alcohol) to yield concentrated protein solutions:

(a) 4 mL: 102 mg/mL rhuMAb HER2, 245 mM trehalose, 21 mM sodium succinate, pH 5.0 or 21 mM histidine, pH 6.0, 0.04% Tween 20™;

(b) 20 mL: 22 mg/mL rhuMAb HER2, 52 mM trehalose, 4 mM sodium succinate, pH 5.0 or 4 mM histidine, pH 6.0, 0.009% Tween 20™.

Figure 1:
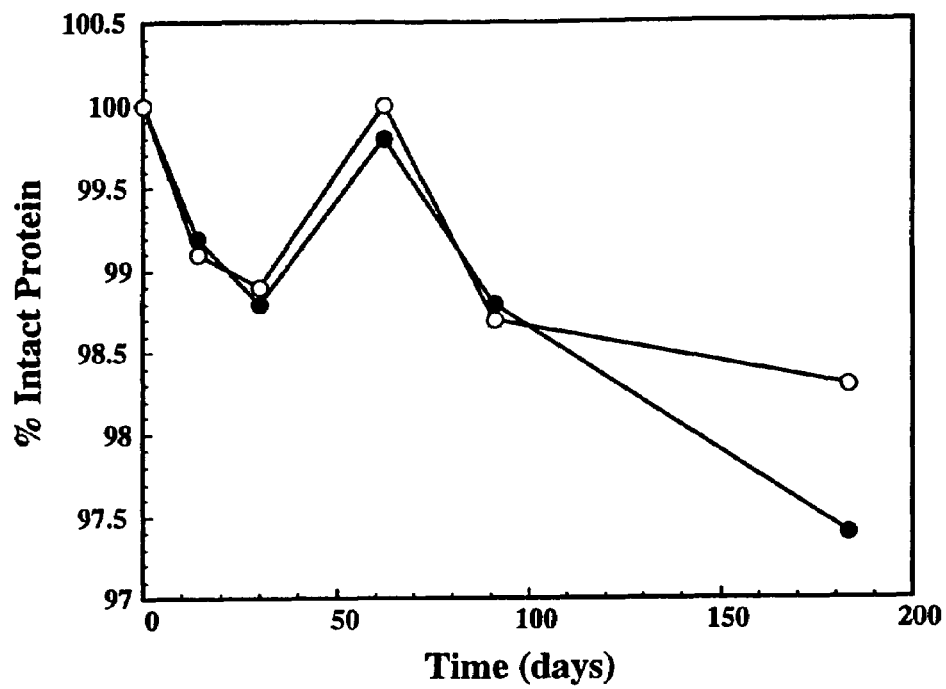
FIG. 1 shows the effect of reconstitution volume on the stability of lyophilized rhuMAb HER2. The lyophilized formulation was prepared from a pre-lyophilization formulation comprising 25 mg/mL protein, 60 mM trehalose, 5 mM sodium succinate, pH 5.0, and 0.01% Tween 20™. The lyophilized cake was incubated at 40° C. and then reconstituted with 4.0 (○) or 20.0 mL (●) of BWFI. The fraction of intact protein in the reconstituted formulation was measured by native size exclusion chromatography and defined as the peak area of the native protein relative to the total peak area including aggregates.

After storage of the lyophilized formulations for 4 weeks at 40° C. and reconstitution to 22 mg/mL protein, the amount of aggregated protein appeared to increase slightly with decreasing trehalose concentration. The stability of the lyophilized protein was not affected by the volume of reconstitution. As shown in FIG. 1, the amount of intact protein after incubation of the lyophilized protein at 40° C. was the same for the 60 mM trehalose, 5 mM sodium succinate, pH 5.0, 0.01% Tween 20™ formulation reconstituted with either 4 or 20 mL of BWFI.

Figure 2:
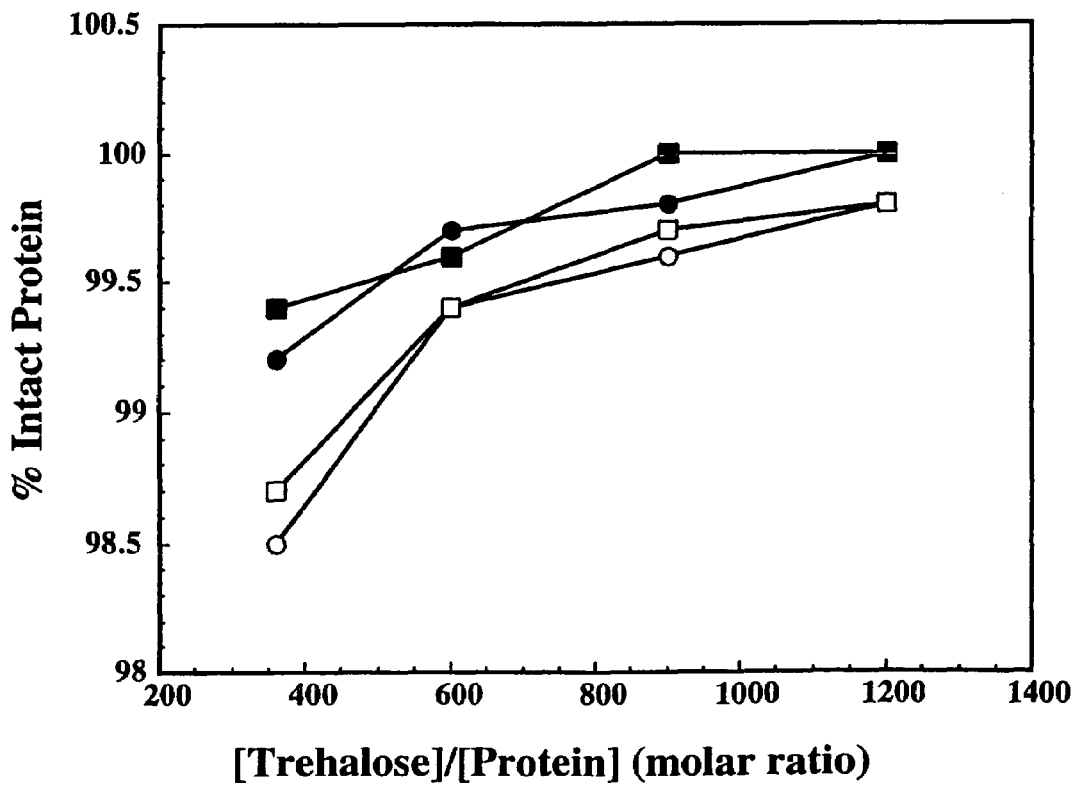
FIG. 2 illustrates the effect of trehalose concentration on the stability of lyophilized rhuMAb HER2. The protein was lyophilized at 25 mg/mL in 5 mM sodium succinate, pH 5.0 (circles) or 5 mM histidine, pH 6.0 (squares) and trehalose concentrations ranging from 60 mM (360 molar ratio) to 200 mM (1200 molar ratio). The lyophilized protein was incubated at 40° C. for either 30 days (closed symbols) or 91 days (open symbols). The amount of intact protein was measured after reconstitution of the lyophilized protein with 20 mL BWFI.

The results shown in Table 3 suggested that there may be a relationship between the trehalose concentration and the protein stability. To further assess this relationship, the formulations containing different concentrations of trehalose formulated in either sodium succinate or histidine were incubated for 91 days at 40° C. The stability was then measured as a function of the trehalose to protein molar ratio for each concentration of trehalose. As shown in FIG. 2, the protein stability clearly decreased with decreasing trehalose concentration for both formulations. There was no apparent difference between the two buffers, succinate and histidine, in these formulations suggesting that the primary stabilizer under these conditions is trehalose. In addition, the observed decrease in intact protein for both these formulations would be acceptable even at the low trehalose concentration for a formulation that is stored at 2-8° C. throughout its shelf-life. However, if controlled room temperature (30° C. maximum temperature) stability is required, higher trehalose concentrations (≧600:1 trehalose:protein) may be needed depending on the stability specifications for the product (i.e. the specification for the amount of intact protein remaining after 2 years of storage). Typically, a controlled room temperature storage condition would require stability for 6 months at 40° C. which is equivalent to storage at 30° C. for 2 years.

Figure 3:
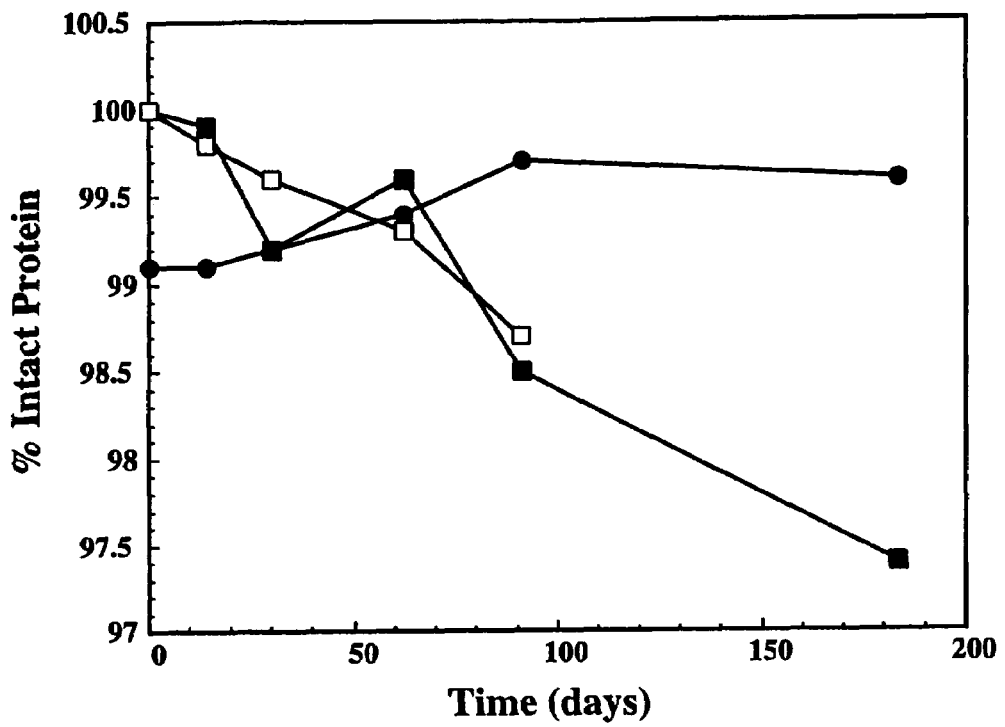
FIG. 3 demonstrates the effect of trehalose concentration on the long term stability of lyophilized rhuMAb HER2 stored at 40° C. The protein was lyophilized at either 25 mg/mL in 5 mM sodium succinate, pH 5.0, 0.01% Tween 20™, and 60 mM trehalose (■) or 5 mM histidine, pH 6.0, 0.01% Tween 20™, and 60 mM trehalose (□) or 21 mg/mL in 10 mM sodium succinate, pH 5.0, 0.2% Tween 20™ and 250 mM trehalose (●). The lyophilized protein was incubated at 40° C. and then reconstituted with 20 mL of BWFI. The amount of intact protein was measured after reconstitution.

As shown in FIG. 3, the 250 mM trehalose formulation was unchanged after 6 months at 40° C. while both the 60 mM trehalose formulations were less stable. The 60 mM trehalose formulations may then require refrigerated storage if the product specification at the end of its shelf-life is, for example, >98% intact protein by native size exclusion chromatography.

Figure 4:
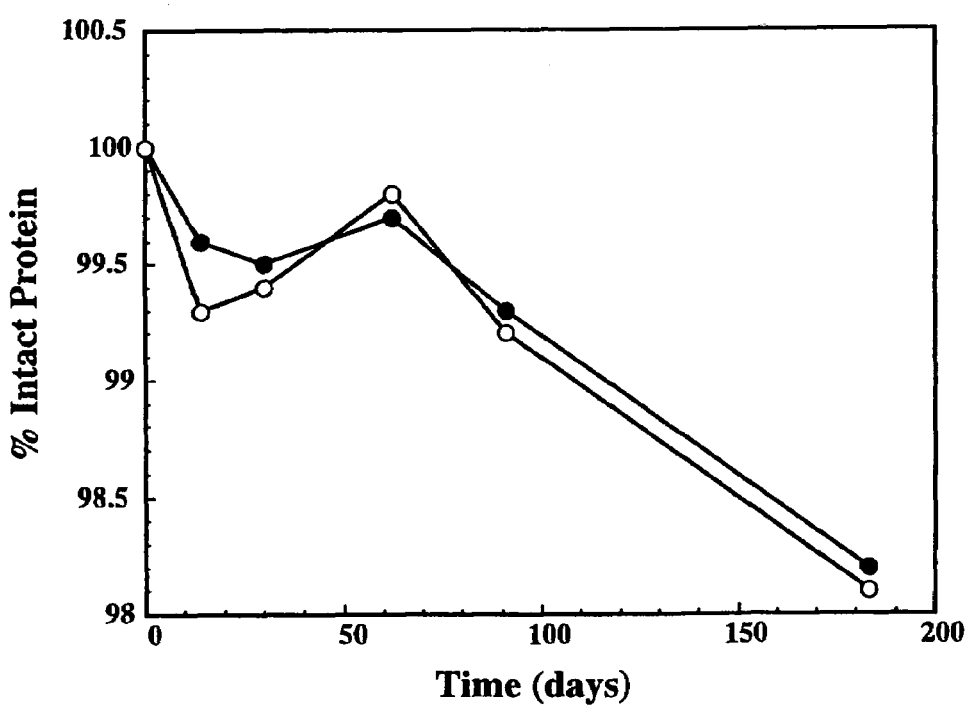
FIG. 4 shows the stability of rhuMAb HER2 lyophilized in 38.4 mM mannitol (7 mg/mL), 20.4 mM sucrose (7 mg/mL), 5 mM histidine, pH 6.0, 0.01% Tween 20™. The lyophilized protein was incubated at 40° C. and then reconstituted with either 4.0 mL (○) or 20 mL (●) of BWFI. The amount of intact protein was measured after reconstitution.

In the previous screening study, sucrose was also observed to prevent aggregation of rhuMAb HER2 after lyophilization and subsequent storage. To achieve isotonic solutions after reconstitution for subcutaneous administration (approximately four-fold concentration of formulation components and protein), the sucrose concentration must be reduced significantly. The equal mass concentration of sucrose and mannitol (bulking agent) used in the screening studies prevented aggregation of the protein. A lower concentration of sucrose and mannitol (equal mass concentrations) was chosen as a potential subcutaneous formulation of rhuMAb HER2. The protein solution (25 mg/mL protein, 5 mM histidine, pH 6.0, 38.4 mM (7 mg/mL) mannitol, 20.4 mM (7 mg/mL) sucrose, 0.01% Tween 20™) was lyophilized in the same manner as the 60 mM trehalose formulation except that the primary drying cycle was extended to 54 hours. After 4 weeks at 40° C., there was a slight increase in the amount of aggregates after reconstitution with 4.0 or 20.0 mL of BWFI (Table 3). The amount of aggregated protein was the same for reconstitution at 22 or 100 mg/mL protein (FIG. 4). Like the 60 mM trehalose formulations, the mannitol/sucrose formulation yielded less intact protein over time at 40° C. The molar ratio of sucrose to protein for this formulation was 120 to 1, indicating that the mannitol/sucrose combination may be more effective than trehalose alone at the same molar ratio of stabilizing sugar (FIGS. 2 and 4).

In the previous examples, the stability of the lyophilized rhuMAb HER2 formulations was determined as a function of temperature. These studies demonstrated that the trehalose and mannitol/sucrose formulations prevented degradation of the protein in the lyophilized state at high temperatures (40° C.). However, these experiments did not address the stability of the protein after reconstitution and storage. Once reconstituted with BWFI, the lyophilized rhuMAb HER2 formulations may be used for several administrations of the drug. In particular, the vial configuration (450 mg rhuMAb HER2) was designed to provide three doses to the average patient (130 mg rhuMAb HER2 per dose). Since the drug is dosed weekly, the vial may be stored at least three weeks after reconstitution. To assure that the rhuMAb HER2 remained stable after reconstitution, stability studies on the reconstituted rhuMAb HER2 formulations were performed at 5° C. and 25° C.

For subcutaneous administration, the formulations were reconstituted to 100 mg/mL (4 mL BWFI). At this high protein concentration, the protein may be more susceptible to aggregation than the intravenous dosage form that was reconstituted to 22 mg/mL protein (20 mL BWFI). The four rhuMAb HER2 formulations from the previous example were assessed for aggregation (loss of intact protein). As shown in Tables 4 through 6, there was no difference in stability for formulations reconstituted at 22 and 100 mg/mL protein. Furthermore, these formulations maintained the protein completely intact for up to 90 days at 5° C. and 30 days at 25° C., indicating that the reconstituted protein could be stored refrigerated for at least 90 days. Unlike the lyophilized protein stability in the previous example, the trehalose concentration in the formulation did not affect the protein stability (Table 7).

TABLE 4

Stability of the reconstituted formulations for rhuMAb HER2 lyophilized at 25 mg/mL protein in 5 mM sodium succinate, pH 5.0, 60 mM trehalose, 0.01% Tween 20 ™

| Time | % Intact Protein | | | |
|---|---|---|---|---|
| | 22 mg/mL protein | | 100 mg/mL protein | |
| (days) | 5° C. | 25° C. | 5° C. | 25° C. |
| 0 | 99.9 | 99.9 | 99.7 | 99.7 |
| 14 | ND | 100.0 | ND | 100.0 |
| 30 | 100.0 | 100.0 | 100.0 | 100.0 |
| 91 | 99.8 | ND | 100 | ND |

The samples were reconstituted with 4.0 or 20.0 mL of BWFI (1.1% or 0.9% benzyl alcohol), and then stored at 5° C. or 25° C. The % intact protein was defined as the fraction of native peak area as measured by native size exclusion chromatography.
ND = not determined.

TABLE 5

Stability of the reconstituted formulations for rhuMAb HER2 lyophilized at 25 mg/mL protein in 5 mM histidine, pH 6.0, 60 mM trehalose, 0.01% Tween 20 ™

| Time | % Intact Protein | | | |
|---|---|---|---|---|
| | 22 mg/mL protein | | 100 mg/mL protein | |
| (days) | 5° C. | 25° C. | 5° C. | 25° C. |
| 0 | 100.0 | 100.0 | 100.0 | 100.0 |
| 14 | ND | 100.0 | ND | 100.0 |
| 31 | 99.3 | 99.7 | 100.0 | 100.0 |
| 61 | 100.0 | ND | ND | ND |

The samples were reconstituted with 4.0 or 20.0 mL of BWFI (1.1% or 0.9% benzyl alcohol), and then stored at 5° C. or 25° C. The % intact protein was defined as the fraction of native peak area as measured by native size exclusion chromatography.
ND = not determined.

TABLE 6

Stability of the reconstituted formulations for rhuMAb HER2 lyophilized at 25 mg/mL protein in 5 mM histidine, pH 6.0, 38.4 mM mannitol, 20.4 mM sucrose, 0.01% Tween 20 ™

| Time | % Intact Protein | | | |
|---|---|---|---|---|
| | 22 mg/mL protein | | 100 mg/mL protein | |
| (days) | 5° C. | 25° C. | 5° C. | 25° C. |
| 0 | 99.7 | 99.7 | 99.8 | 99.8 |
| 14 | ND | 100.0 | ND | 99.8 |
| 31 | 100.0 | 100.0 | 100.0 | 100.0 |
| 92 | 100.0 | ND | 100.0 | ND |

The samples were reconstituted with 4.0 or 20.0 mL of BWFI (1.1% or 0.9% benzyl alcohol), and then stored at 5° C. or 25° C. The % intact protein was defined as the fraction of native peak area as measured by native size exclusion chromatography.
ND = not determined.

TABLE 7

Stability of the reconstituted formulations for rhuMAb HER2 lyophilized at 21 mg/mL protein in 10 mM sodium succinate, pH 5.0, 250 mM trehalose, 0.2% Tween 20 ™

| Time | % Intact Protein 21 mg/mL protein | |
|---|---|---|
| (days) | 5° C. | 25° C. |
| 0 | 99.8 | 99.8 |
| 14 | ND | 100.0 |
| 31 | 99.9 | 99.4 |
| 92 | 99.8 | ND |

The samples were reconstituted with 20.0 mL of BWFI (0.9% benzyl alcohol), and then stored at 5° C. or 25° C. The % intact protein was defined as the fraction of native peak area as measured by native size exclusion chromatography.
ND = not determined.

As mentioned previously, the major degradation route for rhuMAb HER2 in aqueous solutions is deamidation or succinimide formation. The loss of native protein due to deamidation or succinimide formation was assessed for the four reconstituted rhuMAb HER2 formulations.

Analysis of rhuMAb HER2 deamidation and succinimide formation was performed using cation exchange chromatography. A Bakerbond Wide-Pore Carboxy Sulfon (CSX) column (4.6×250 mm) was operated at a flow rate of 1 mL/min. The mobile phase buffers were (A) 0.02 M sodium phosphate, pH 6.9, and (B) 0.02 M sodium phosphate, pH 6.9, 0.2 M NaCl. The chromatography was then performed at 40° C. follows:

TABLE 8

| Time (min) | % Buffer B |
|---|---|
| 0 | 10 |
| 55 | 45 |
| 57 | 100 |
| 62 | 100 |
| 62.1 | 10 |
| 63 | 10 |

Peak elution was monitored at 214 nm and 75 µg of protein was loaded for each analysis.

Figure 5:
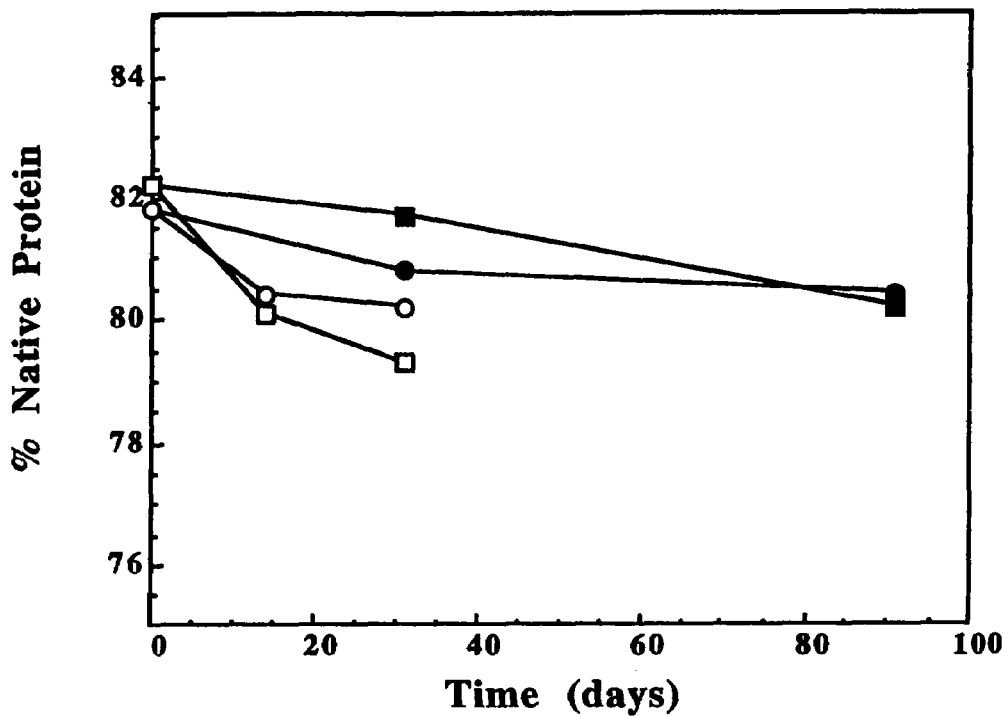
FIG. 5 demonstrates stability of reconstituted rhuMAb HER2 lyophilized in 5 mM sodium succinate, pH5.0, 60 mM trehalose, 0.01% Tween 20™. Samples were reconstituted with either 4.0 mL (squares) or 20.0 mL (circles) of BWFI (20 mL:0.9% benzyl alcohol; 4 mL:1.1% benzyl alcohol) and then stored at 5° C. (solid symbols) or 25° C. (open symbols). The % native protein was defined as the peak area of the native (not degraded) protein relative to the total peak area as measured by cation exchange chromatography.
Figure 6:
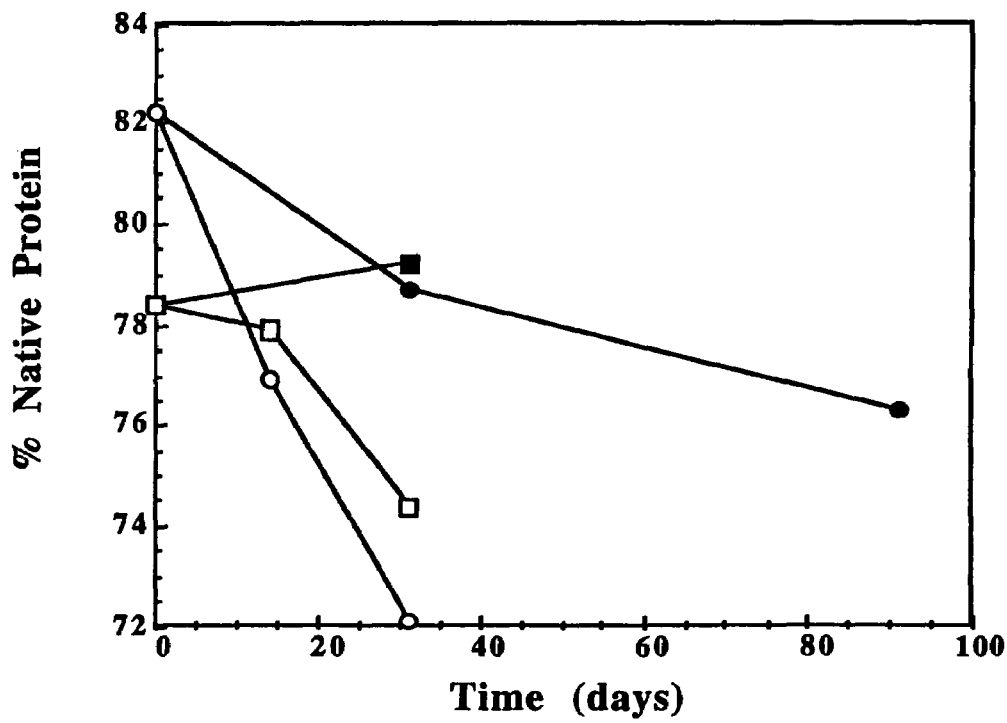
FIG. 6 shows stability of reconstituted rhuMAb HER2 lyophilized in 5 mM histidine, pH 6.0, 60 mM trehalose, 0.01% Tween 20. Samples were reconstituted with either 4.0 mL (squares) or 20.0 mL (circles) of BWFI (20 mL:0.9% benzyl alcohol; 4 mL:1.1% benzyl alcohol) and then stored at 5° C. (solid symbols) or 25° C. (open symbols). The % native protein was defined as the peak area of the native (not degraded) protein relative to the total peak area as measured by cation exchange chromatography.
Figure 7:
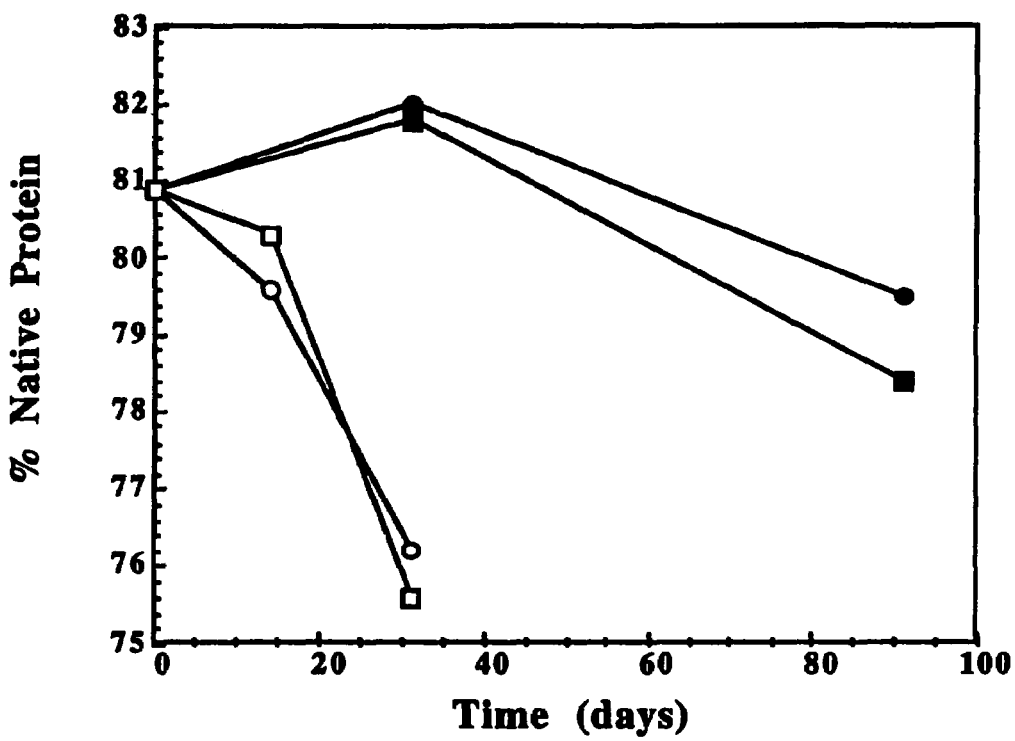
FIG. 7 reveals stability of reconstituted rhuMAb HER2 lyophilized in 5 mM histidine, pH 6.0, 38.4 mM mannitol, 20.4 mM sucrose, 0.01% Tween 20. Samples were reconstituted with either 4.0 mL (squares) or 20.0 mL (circles) of BWFI (20 mL:0.9% benzyl alcohol; 4 mL:1.1% benzyl alcohol) and then stored at 5° C. (solid symbols) or 25° C. (open symbols). The % native protein was defined as the peak area of the native (not degraded) protein relative to the total peak area as measured by cation exchange chromatography.
Figure 8:
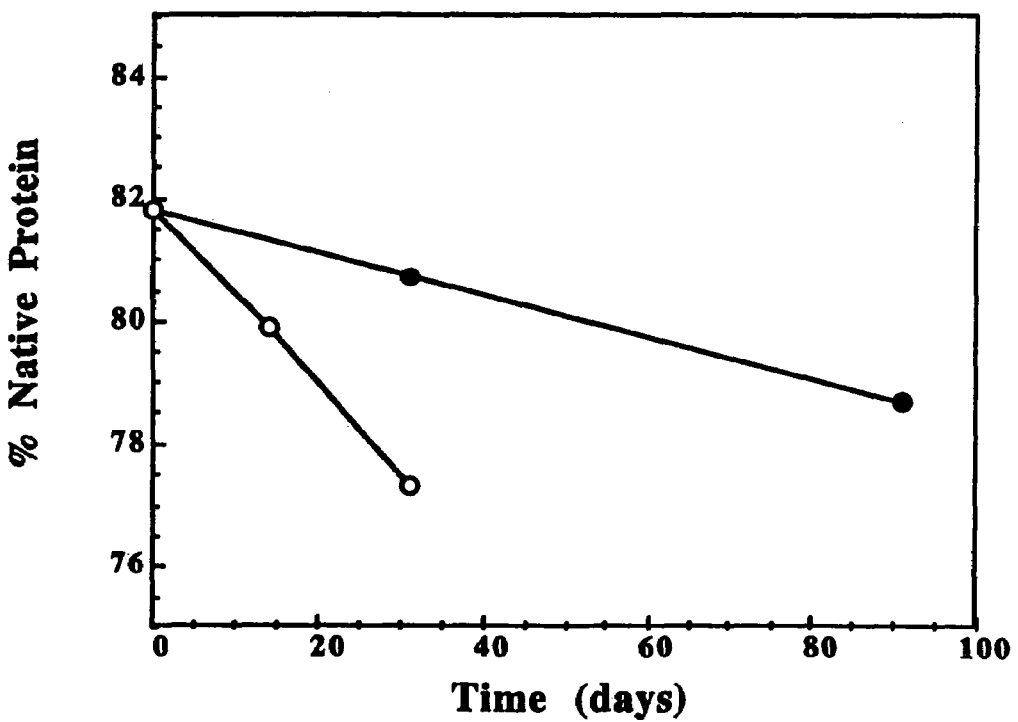
FIG. 8 shows stability of reconstituted rhuMAb HER2 lyophilized in 10 mM sodium succinate, pH 5.0, 250 mM trehalose, 0.2% Tween 20. Samples were reconstituted with 20.0 mL of BWFI (0.9% benzyl alcohol) and then stored at 5° C. (●) or 25° C. (○). The % native protein was defined as the peak area of the native (not degraded) protein relative to the total peak area as measured by cation exchange chromatography.

Again, there were no differences in stability of the formulations reconstituted at 22 and 100 mg/mL protein (FIG. 5 through 7). The protein degradation was more rapid at 25° C. than 5° C. for each formulation, and the rate of degradation was comparable for all the formulations stored at 5° C. The formulations containing histidine underwent a slightly greater rate of degradation at 25° C. than the succinate formulations. The amount of trehalose in the formulation did not affect the degradation rate at either temperature (FIGS. 5 and 8). These results indicated that these four formulations provide an acceptable rate of degradation under refrigerated storage conditions (5° C.) for the intended period of use (30 days after reconstitution with BWFI).

Multi-use formulations should pass preservative efficacy testing as described by the US Pharmacopeia (USP) for use in the United States. The rhuMAb HER2 lyophilized formulation consisting of 25 mg/mL protein, 5 mM histidine, pH 6.0, 60 mM trehalose, 0.01% Tween 20™ was reconstituted with 20 mL of benzyl alcohol at concentrations between 0.9 and 1.5% w/w. For concentrations at or above 1.3% w/w, the reconstituted solution became cloudy after overnight incubation at room temperature (~25° C.). Reconstitution with the standard BWFI solution (0.9% benzyl alcohol) resulted in a solution that did not consistently pass the preservative challenge tests. However, reconstitution with 1.0 or 1.1% benzyl alcohol was both compatible with the formulation and passed the preservative challenge testing. The manufacturer's specifications for the solution required a range of ±10%, and therefore, the lyophilized formulations are reconstituted with 1.1% benzyl alcohol (1.1±0.1%).

A single step lyophilization cycle for the rhuMAb HER2 formulation was developed. In the single step lyophilization cycle, rhuMAb HER2 at 25 mg/mL, 60 mM trehalose, 5 mM histidine pH 6 and 0.01% polysorbate 20 was lyophilized at a shelf temperature of 20° C., and a pressure of 150 mTorr. After 47 hours, the residual moisture content of the lyophilized cake was less than 5%. This lyophilization cycle is considered to be useful in that it simplifies the manufacturing process, by eliminating the secondary drying step.

Example 2

Anti-IgE Formulation

IgE antibodies bind to specific high-affinity receptors on mast cells, leading to mast cell degranulation and release of mediators, such as histamine, which produce symptoms associated with allergy. Hence, anti-IgE antibodies that block binding of IgE to its high-affinity receptor are of potential therapeutic value in the treatment of allergy. These antibodies must also not bind to IgE once it is bound to the receptor because this would trigger histamine release. This example describes the development of a lyophilized formulation comprising full length humanized anti-IgE antibody MaE11 described in Presta et al. *J. Immunology*, 151: 2623-2632 (1993).

Materials: Highly purified rhuMAb E25 (recombinant humanized anti-IgE antibody MaE11) which did not contain Tween 20™ was used in the formulations described below. Spectra/Por 7 dialysis membranes were purchased from Spectrum (Los Angeles, Calif.). All other reagents used in this study were obtained from commercial sources and were of analytical grade. Formulation buffers and chromatography mobile phase were prepared by mixing the appropriate amount of buffer and salt with Milli-Q water in a volumetric flask.

Formulation: E25 S Sepharose pool was dialyzed into formulation buffers as specified. Dialysis was accomplished by a minimum of 4×2 L buffer exchanges over a 48 hour period at 2-8° C. Following dialysis, lyoprotectant was added at a isotonic concentration to some of the formulations as required. Protein concentration following dialysis was determined by UV spectroscopy using a molar absorptivity of 1.60. The dialyzed protein was diluted to the predetermined formulation concentration with an appropriate formulation buffer, sterile filtered using a 0.22 µm Millex-GV filter (Millipore) and dispensed into pre-washed and autoclaved glass vials. The vials were fitted with siliconized teflon lyophilization stoppers and lyophilized using the following conditions: the E25 formulation was frozen to −55° C. at 80° C./hour and the vial content was kept frozen for 4 hours. The shelf temperature was ramped to 25° C. at 10° C./hour for primary drying. Primary drying was carried out at 25° C., 50µ chamber vacuum pressure for 39 hours such that the residual moisture of the lyophilized cake was 1-2%. Following lyophilization, a vial of each formulation was removed for t=0 analysis and the remaining vials were held at various temperatures which include −70° C., 2-8° C., 25° C., 30° C. (controlled room temperature) 40° C. and 50° C.

Chromatography: Native size exclusion chromatography was carried out on a Bio-Rad Bio-Select™ SEC 250-5 column (300×7.8 mm). The column was equilibrated and ran in PBS at a flow rate of 0.5 mL/min using a Hewlett Packard 1090 L HPLC equipped with a diode array detector. Molecular weight standards (Bio-Rad, Inc.) consisting of thyroglobulin (670 kd), gamma-globulin (158 kd), ovalbumin (44 kd), and cyanocobalamin (1.35 kd) were used to calibrate the column. The sample load was 25 μg and protein was detected by monitoring the UV absorption at 214 nm using Turbochrom 3 software (PE Nelson, Inc).

Hydrophobic Interaction Chromatography: F(ab')$_2$ fragments of the E25 antibody were chromatographed using a TosoHaas Butyl-NPR column (3.5×4.6 mm) and a Hewlett Packard 1090 L HPLC equipped with a diode array detector. Elution buffer A was: 20 mM Tris, 2 M ammonium sulfate, 20% (v/v) glycerol, pH 8.0 while elution buffer B was: 20 mM Tris, 20% (v/v) glycerol, pH 8.0. The column was equilibrated with 10% elution buffer B at a flow rate of 1.0 mL/min for a minimum of 20 minutes. The sample load was 5 μg and protein was detected by monitoring the UV absorption at 214 nm using Turbochrom 3 data acquisition software (PE Nelson, Inc). Following injection of the sample, the column was maintained at 10% buffer B for 1 minute followed by a linear gradient of from 10% to 62% buffer B in 20 minutes. The column was washed with 100% buffer B for 5 minutes and re-equilibrated with 10% buffer B for a minimum of 20 minutes between successive sample injections.

Antibody Binding Activity: IgE receptor binding inhibition assay (IE25:2) was carried out as described in Presta et al., supra, on samples diluted to 20 μg/mL and 30 μg/mL in assay diluent (phosphate buffered saline, 0.5% BSA, 0.05% polysorbate 20, 0.01% Thimerosol). Each dilution was then assayed in triplicate and the results were multiplied by an appropriate dilution factor to yield an active concentration. The results from 6 assays were averaged. The assay measures the ability of rhuMAb E25 to competitively bind to IgE and thereby prevent IgE from binding to its high affinity receptor which is immobilized to an ELISA plate. The results are divided by the antibody concentration as determined by UV absorption spectroscopy and reported as a specific activity. Previous experiments have shown that this assay is stability indicating.

Particulate Assay: Reconstituted vials of lyophilized rhuMAb E25 were pooled to achieve a volume of approximately 7 mL. A count of the number of particles of size ranging from 2 to 80 μm present in 1 mL of sample was determined using a Hiac/Royco model 8000 counter. The counter was first washed with 1 mL of sample three times followed by the measurement of 1 mL of sample in triplicate. The instrument determines the number of particles per mL that are equal to or greater than 10 μm and the number of particles per mL that are equal to or greater than 25 μm.

Figure 9:
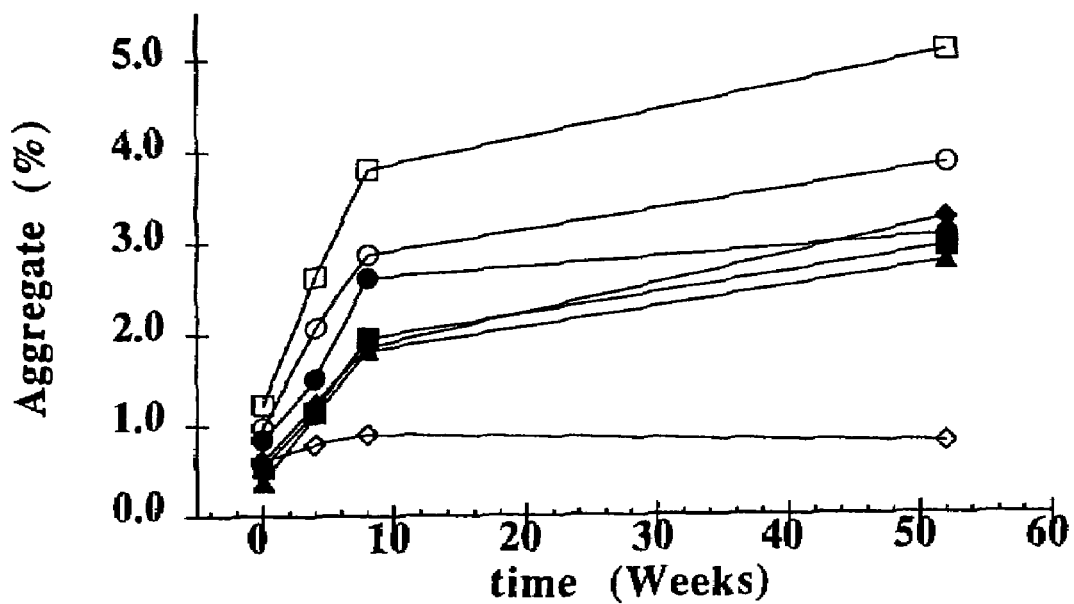
FIG. 9 shows aggregation of rhuMAb E25 formulated into buffers ranging from pH 5 to pH 7 at 10 mM buffer concentration and 5 mg/mL antibody concentration. Samples were lyophilized and assayed at time zero and after 4 weeks, 8 weeks, and 52 weeks of storage at 2-8° C. The buffers were: potassium phosphate pH 7.0 (○); sodium phosphate pH 7.0 (□); histidine pH 7.0 (◇); sodium succinate pH 6.5 (●); sodium succinate pH 6.0 (■); sodium succinate pH 5.5 (◆); and sodium succinate pH 5.0 (▲).
Figure 10:
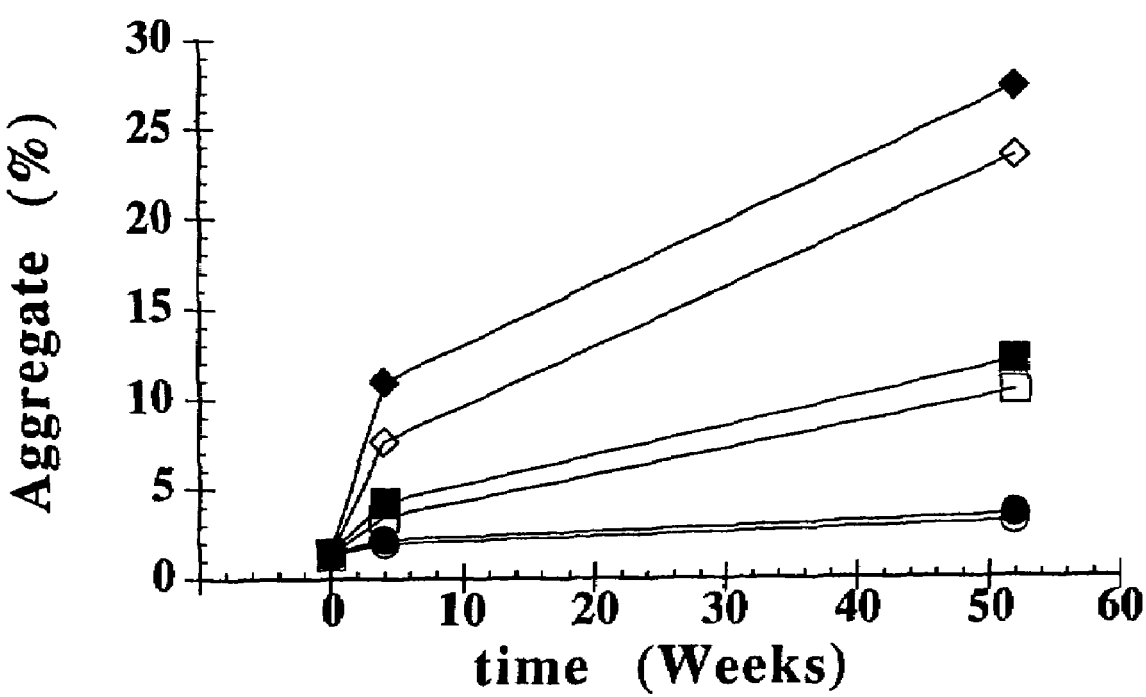
FIG. 10 depicts aggregation of rhuMAb E25 lyophilized in 5 mM histidine buffer at both pH 6 and pH 7 and assayed following storage as follows. The buffer was at: pH 6.0 stored at 2-8° C. (○); pH 6 stored at 25° C. (□); pH 6 stored at 40° C. (◇); pH 7 stored at 2-8° C. (●); pH 7 stored at 25° C. (■); and pH 7 stored at 40° C. (◆).

The first step in the development of a formulation for the anti-IgE antibody was to determine a suitable buffer and pH for lyophilization and storage of the product. Antibody at a concentration of 5.0 mg/mL was formulated into 10 mM succinate buffers ranging from pH 5.0 to pH 6.5 and into sodium phosphate, potassium phosphate and histidine buffers at pH 7.0. FIG. 9 shows increased antibody aggregate was observed in the higher pH formulations both before and after lyophilization. An exception was the histidine formulation at pH 7, where no increase in aggregate was observed upon storage at 2-8° C. FIG. 10 shows rhuMAb E25 lyophilized in 5 mM histidine buffer at both pH 6 and pH 7 and stored for 1 year at 2-8° C., 25° C., and 40° C. At each assay time point and storage temperature the pH 6 formulation had less aggregate than the antibody formulated at pH 7. These results show histidine at pH 6 is a particularly useful buffer system for preventing aggregation of the antibody.

To facilitate screening of lyoprotectants, the anti-IgE antibody was formulated into sodium succinate at pH 5 with or without a lyoprotectant. Potential lyoprotectants, added at isotonic concentrations, were grouped into 3 categories:

(a) non-reducing monosaccharide (i.e. mannitol);
(b) reducing disaccharides (i.e. lactose and maltose); and
(c) non-reducing disaccharides (i.e. trehalose and sucrose).

Figure 11:
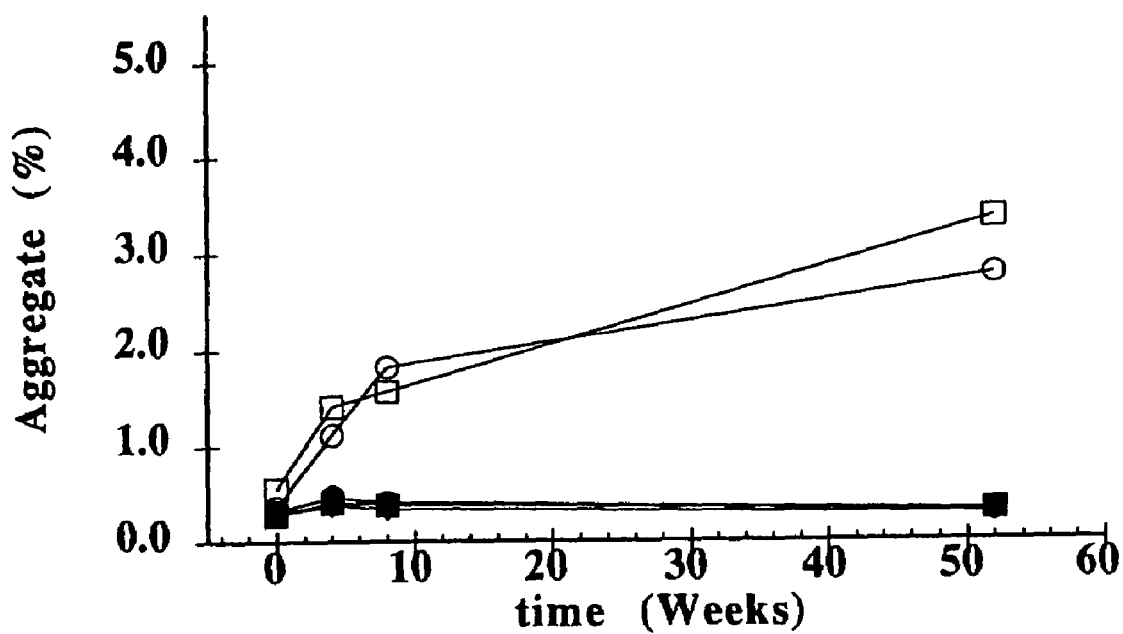
FIG. 11 illustrates aggregation of 5 mg/mL rhuMAb E25 formulated into 10 mM sodium succinate at pH 5.0 with lyoprotectant added at a concentration of 275 mM (isotonic). The lyoprotectants were: control, no lyoprotectant (○); mannitol (□); lactose (◇); maltose (●); trehalose (■); and sucrose (◆). Samples were lyophilized and assayed at time zero and after 4 weeks, 8 weeks, and 52 weeks of storage at 2-8° C.
Figure 12:
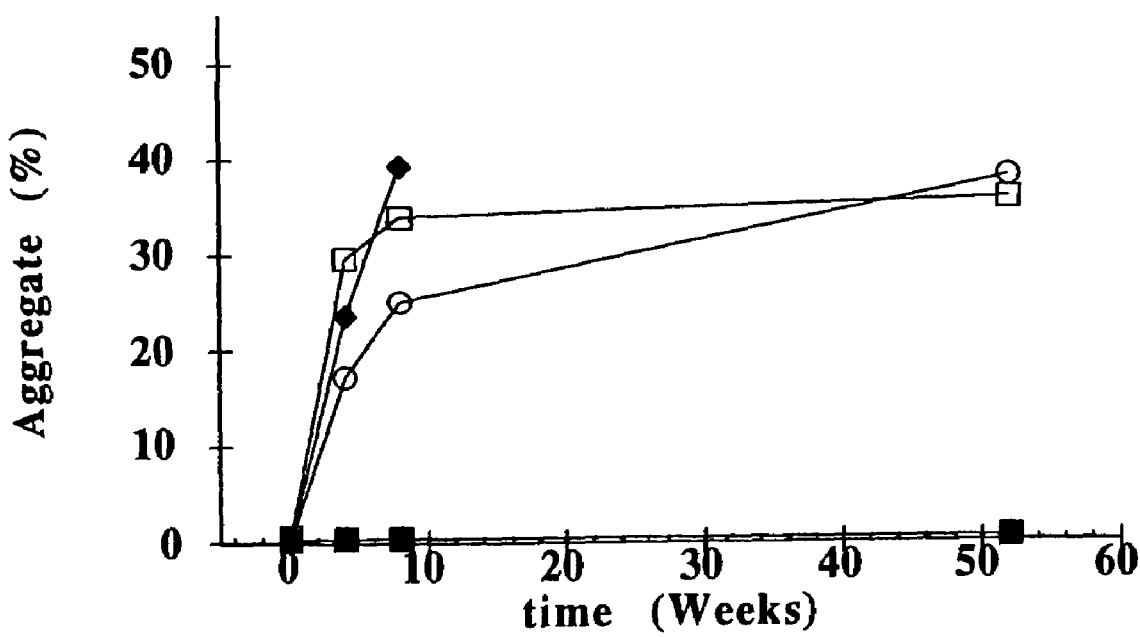
FIG. 12 shows aggregation of 5 mg/mL rhuMAb E25 formulated into 10 mM sodium succinate at pH 5.0 with lyoprotectant added at a concentration of 275 mM (isotonic). The lyoprotectants were: control, no lyoprotectant (○); mannitol (□); lactose (◇); maltose (●); trehalose (■); and sucrose (◆). Samples were lyophilized and assayed at time zero and after 4 weeks, 8 weeks, and 52 weeks of storage at 40° C.

Aggregation of the formulations following storage at 2-8° C. and 40° C. for one year is shown in FIGS. 11 and 12. With storage at 2-8° C., the monosaccharide formulation (mannitol) aggregated at a rate similar to the buffer control, while formulations containing the disaccharides were equally effective in controlling aggregation (FIG. 11). The results following storage at 40° C. where similar with the exception of the sucrose formulation which rapidly aggregated (which correlated with a browning of the freeze-dried cake (FIG. 12)). This was later shown to be caused by degradation of sucrose following storage at both acidic pH and high temperature.

Figure 13:
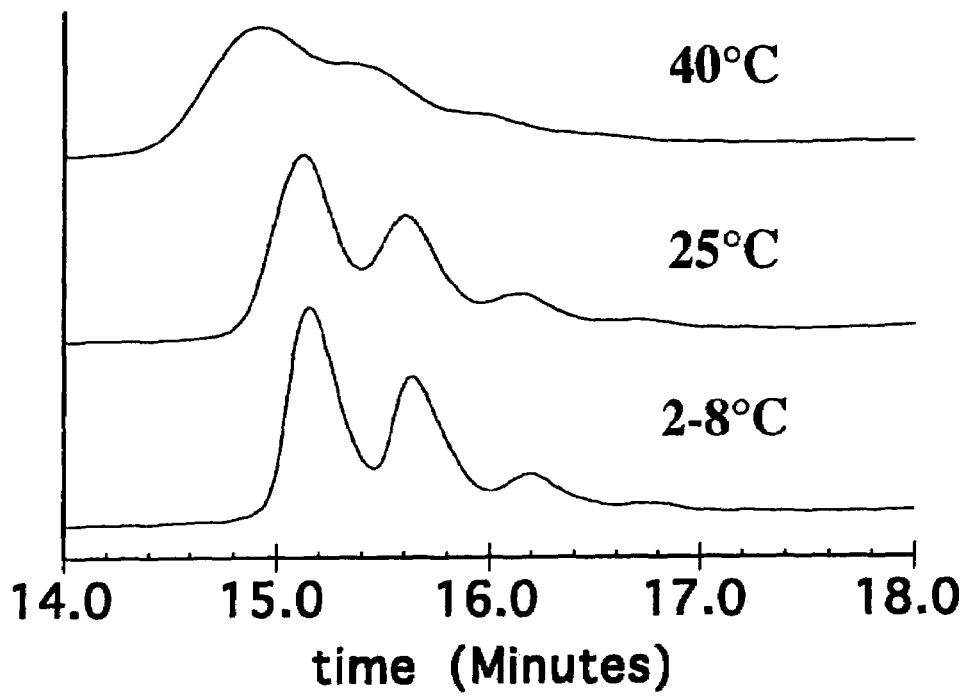
FIG. 13 depicts hydrophobic interaction chromatography of 20 mg/mL rhuMAb E25 lyophilized in histidine buffer at pH 6 with an isotonic concentration (i.e. 275 mM) of lactose stored for 24 weeks at 2-8, 25 or 40° C. and reconstituted to 20 mg/mL.
Figure 14:
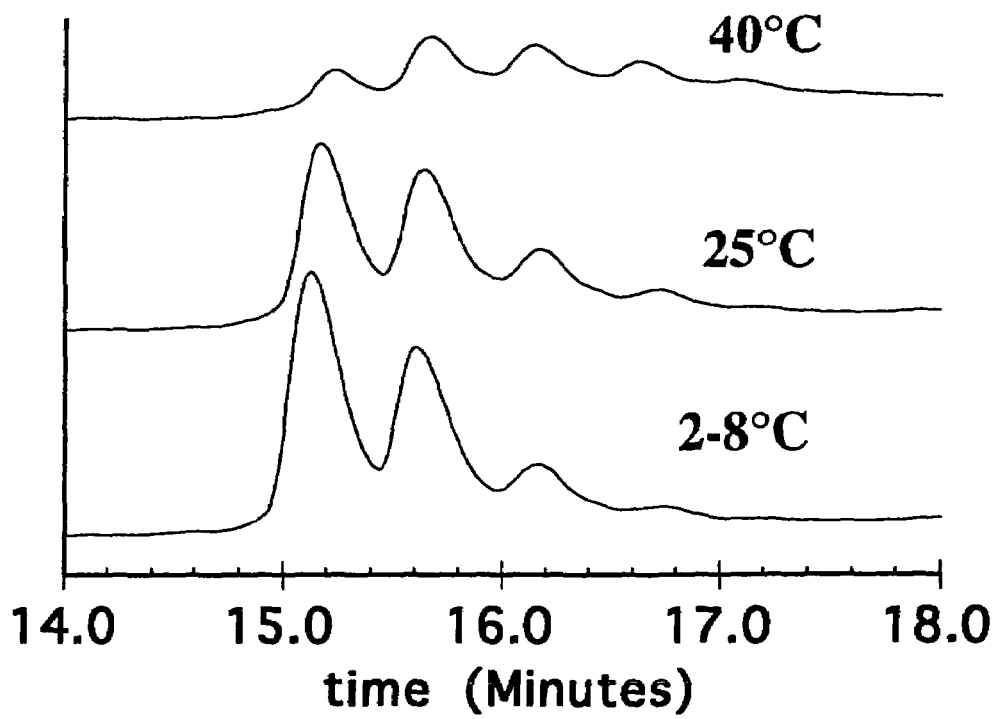
FIG. 14 shows hydrophobic interaction chromatography of 20 mg/mL rhuMAb E25 lyophilized in histidine buffer at pH 6 stored for 24 weeks at 2-8, 25 or 40° C. and reconstituted to 20 mg/mL.
Figure 15:
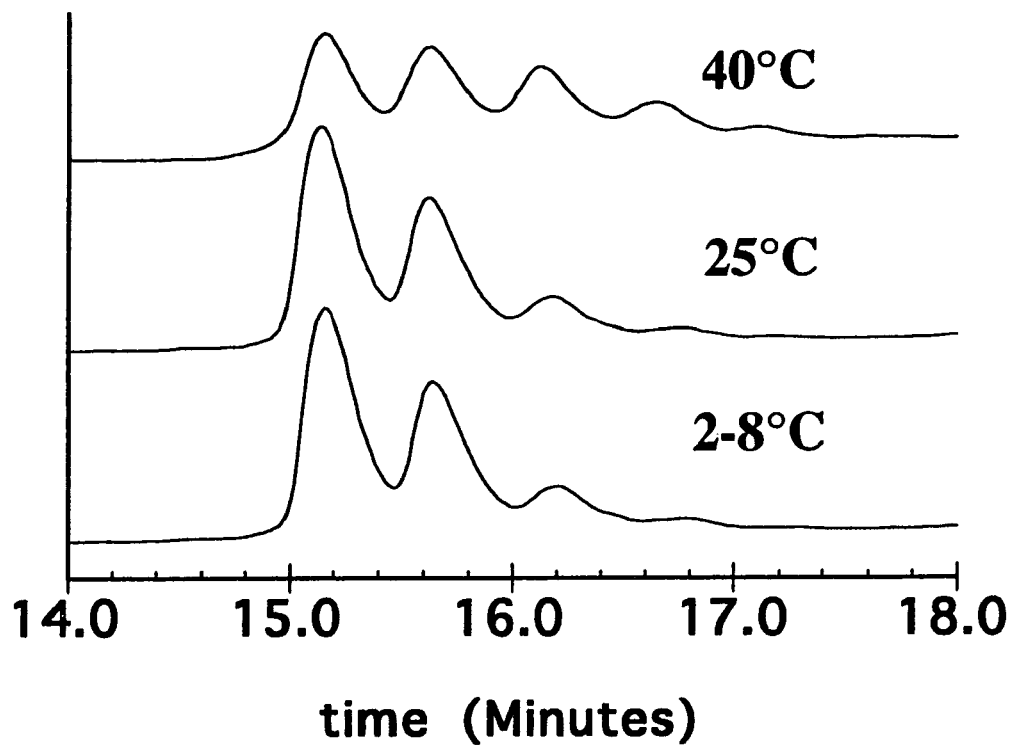
FIG. 15 illustrates hydrophobic interaction chromatography of 20 mg/mL rhuMAb E25 lyophilized in histidine buffer at pH 6 with an isotonic concentration (i.e. 275 mM) of sucrose and stored for 24 weeks at 2-8, 25 or 40° C. and reconstituted to 20 mg/mL.

Hydrophobic interaction chromatography of the antibody formulated in histidine buffer at pH 6 with lactose shows the antibody is altered following storage for 6 months at 40° C. (FIG. 13). The chromatography peaks are broadened and the retention time decreases. These changes are not observed with the buffer control and sucrose formulations stored under similar conditions as shown in FIGS. 14 and 15, respectively. Furthermore, isoelectric focusing showed an acidic shift in the pI of the antibody formulated in lactose and stored at 25° C. and 40° C. This indicates that reducing sugars are not suitable as lyoprotectants for the antibody.

Figure 16:
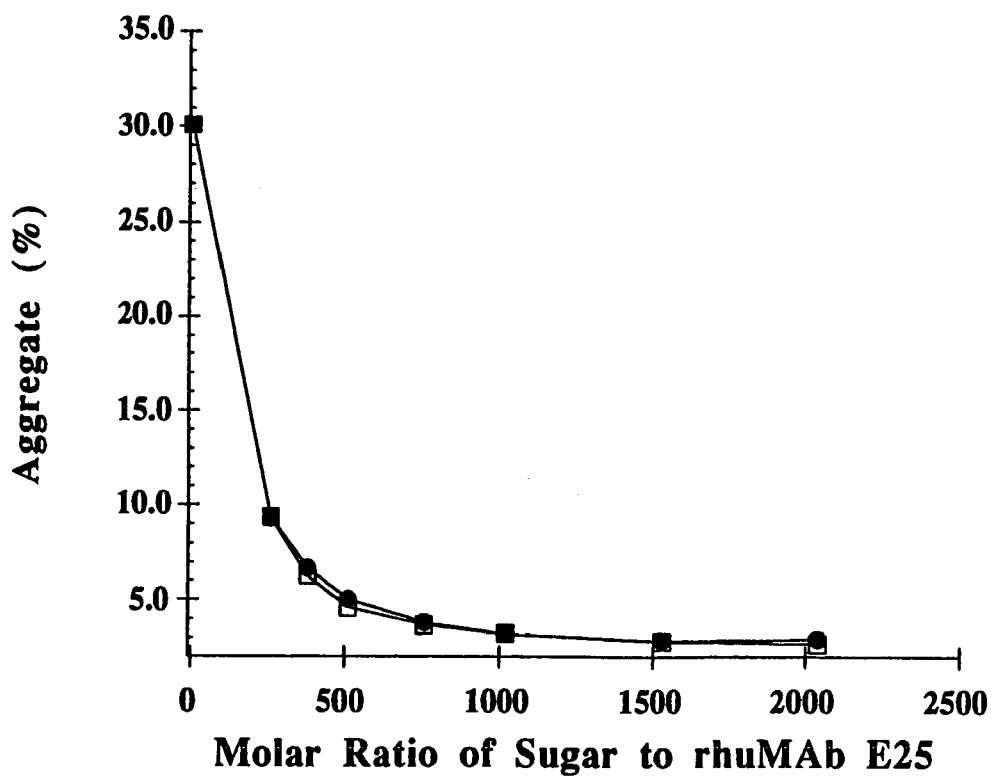
FIG. 16 illustrates the effect of sugar concentration on rhuMAb E25 formulated at 20 mg/mL in 5 mM histidine at pH 6.0. Sucrose (●) and trehalose (□) were added to the formulation at molar ratios ranging from 0 to 2010 (isotonic) (see Table 1 below). Samples were lyophilized and assayed after 12 weeks of storage at 50° C.

Aggregation of lyophilized formulations of anti-IgE at a concentration of 20 mg/mL in 5 mM histidine buffer at pH 6 with various concentrations of sucrose and trehalose following storage for 12 weeks at 50° C. is shown in FIG. 16. Both sugars have a similar protective effect on aggregation when the sugar concentration is greater than 500 moles of sugar per mole of antibody. From these results, isotonic and hypertonic formulations of both sucrose and trehalose were identified for further development. The formulations are designed to be filled prior to lyophilization at a relatively low concentration of antibody and the lyophilized product is reconstituted with less volume than was filled with bacteriostatic water for injection (BWFI) comprising 0.9% benzyl alcohol. This allows the concentration of the antibody immediately prior to subcutaneous delivery and includes a preservative for a potential multi-use formulation while avoiding interactions between the protein and preservative upon long-term storage.

Isotonic formulation: Anti-IgE at 25 mg/mL formulated in 5 mM histidine buffer at pH 6 with 500 moles of sugar per mole antibody which equals a sugar concentration of 85 mM. This formulation is reconstituted with BWFI (0.9% benzyl alcohol) at a volume which is four times less than was filled. This results in a 100 mg/mL of antibody in 20 mM histidine at pH 6 with an isotonic sugar concentration of 340 mM.

Hypertonic formulation: Anti-IgE at 25 mg/mL formulated in 5 mM histidine buffer at pH 6 with 1000 moles of sugar per mole antibody which equals a sugar concentration of 161 mM. This formulation is reconstituted with BWFI (0.9% benzyl alcohol) at a volume which is four times less than was filled. This results in a 100 mg/mL of antibody in 20 mM histidine at pH 6 with a hypertonic sugar concentration of 644 mM.

Comparisons of the antibody aggregation following storage of the isotonic and hypertonic formulations for up to 36 weeks are shown in FIGS. 17 to 19. No change in aggregation is observed in either the hypertonic or isotonic formulations with storage at 2-8° C. (FIG. 17). With storage at controlled room temperature (30° C.) increased aggregation is not observed in the hypertonic formulations while an increase in aggregate of from 1 to 2% occurs in the isotonic formulations (FIG. 18). Finally, following storage at 50° C. a minimal increase in aggregate is observed with the hypertonic formulations, a 4% increase in aggregate occurs with the isotonic trehalose formulation and a 12% increase in aggregate occurs with the isotonic sucrose formulation (FIG. 19). These results show the isotonic formulation contains the minimum amount of sugar necessary to maintain the stability of the antibody with storage at a temperature up to 30° C.

The binding activity of the anti-IgE in the isotonic and hypertonic formulations was measured in an IgE receptor inhibition assay. It was discovered that the binding activity of the isotonic and hypertonic sucrose and trehalose formulations was essentially unchanged following storage at −70° C., 2-8° C., 30° C. and 50° C. for up to 36 weeks.

Lyophilized formulations of proteins are known to contain insoluble aggregates or particulates (Cleland et al., *Critical Reviews in Therapeutic Drug Carrier Systems,* 10 (4):307-377 (1993)). Accordingly, a particulate assay of antibody lyophilized at a concentration of 25 mg/mL in 5 mM histidine, pH 6 with the addition of 85 mM and 161 mM sucrose and trehalose was performed. Polysorbate 20 was added to the formulations at a concentration of 0.005%, 0.01%, and 0.02%. Samples were lyophilized and assayed following reconstitution to 100 mg/mL antibody in 20 mM histidine, pH 6 with 340 mM and 644 mM sugar. The polysorbate 20 concentration following reconstitution was 0.02%, 0.04%, and 0.08%.

Table 9 below shows the number of particles of size equal to or greater than 10 µm and equal to or greater than 25 µm from the isotonic and hypertonic sucrose and trehalose formulations. Polysorbate 20 was added to the formulations at concentrations of 0.005%, 0.01%, and 0.02% prior to lyophilization. The results show that the addition of Tween™ to the formulation significantly reduces the number of particles in each size range tested. The US Pharmacopeia (USP) specification for small volume injections are not more than 6,000 particles of greater than or equal to 10 µm and not more than 600 particles of greater than or equal to 25 µm per container (Cleland et al., supra). With the addition of polysorbate 20, both the hypertonic and isotonic formulations pass this specification.

TABLE 9

| Formulation | Polysorbate 20 | Particles per mL ≧10 µm | ≧25 µM |
|---|---|---|---|
| Isotonic Sucrose | None | 16,122 | 28 |
| | 0.005% | 173 | 2 |
| | 0.01% | 224 | 5 |
| | 0.02% | 303 | 6 |
| Hypertonic Sucrose | None | 14,220 | 84 |
| | 0.005% | 73 | 6 |
| | 0.01% | 51 | 0 |
| | 0.02% | | 6 |
| Isotonic Trehalose | None | 33,407 | 24 |
| | 0.005% | 569 | 4 |
| | 0.01% | 991 | 16 |
| | 0.02% | 605 | 9 |
| Hypertonic Trehalose | None | 24,967 | 28 |
| | 0.005% | 310 | 11 |
| | 0.01% | 209 | 6 |
| | 0.02% | 344 | 6 |

One formulation developed for the anti-IgE antibody (i.e. 143 mg vial isotonic formulation of rhuMAb E25) which is considered to be useful for subcutaneous delivery of this antibody is shown in Table 10 below. A 10 cc vial is filled with 5.7 mL of rhuMAb E25 at a concentration of 25 mg/mL formulated in 5 mM histidine at pH 6.0 with 0.01% polysorbate 20. Sucrose is added as a lyoprotectant at a concentration of 85 mM which corresponds to a molar ratio of sugar to antibody of 500 to 1. The vial is lyophilized and reconstituted with 0.9% benzyl alcohol to one quarter of the volume of the fill or 1.2 mL. The final concentration of components in the formulation is increased four fold to 100 mg/mL rhuMAb E25 in 20 mM histidine at pH 6 with 0.04% polysorbate 20 and 340 mM sucrose (isotonic) and 0.9% benzyl alcohol. The formulation contains histidine buffer at pH 6 because of its demonstrated protective effect on antibody aggregation. Sucrose was added as the lyoprotectant because of previous use in the pharmaceutical industry. The concentration of sugar was chosen to result in an isotonic formulation upon reconstitution. Finally, polysorbate 20 is added to prevent the formation of insoluble aggregates.

TABLE 10

| Pre-lyophilized Formulation (Fill 5.7 mL into 10 cc vial) | Reconstituted Formulation (1.2 mL 0.9% Benzyl Alcohol) |
|---|---|
| 25 mg/mL rhuMAb E25 | 100 mg/mL rhuMAb E25 |
| 5 mM Histidine, pH 6.0 | 20 mM Histidine, pH 6.0 |
| 85 mM Sucrose | 340 mM Sucrose |
| 0.01% Polysorbate 20 | 0.04% Polysorbate 20 |
| — | 0.9% Benzyl Alcohol |

What is claimed is:

1. A formulation comprising a lyophilized mixture of a recombinant humanized HER2 monoclonal antibody, a lyoprotectant, and a buffer.

2. The formulation of claim 1 wherein the pH of the formulation is from 5-7.

3. The formulation of claim 2 wherein the pH of the formulation is 6.0.

4. The formulation of claim 1 wherein the buffer is histidine, phosphate, Tris, citrate, succinate, or other organic acid.

5. The formulation of claim 4 wherein the buffer is histidine.

6. The formulation of claim 1 wherein the antibody is huMAb4D5-8.

7. The formulation of claim 1 further comprising a surfactant.

8. The formulation of claim 7 wherein the surfactant is a nonionic surfactant.

9. The formulation of claim 7 wherein the surfactant is a polysorbate.

10. The formulation of claim 1 wherein the lyoprotectant is a sugar.

11. The formulation of claim 1 which is stable at 30° C. for at least 6 months.

12. The formulation of claim 1 wherein the concentration of the humanized HER2 antibody is from about 5-40 mg/mL.

13. The formulation of claim 12 wherein the concentration of the humanized HER2 antibody is from about 20-30 mg/mL.

14. A vial containing a formulation comprising a lyophilized mixture of a recombinant humanized HER2 monoclonal antibody, a lyoprotectant, and a buffer.

15. The vial of claim 14 which is a 3, 5, 10, 20, 50, or 100 cc vial.

16. The vial of claim 14 wherein the antibody is huMAb4D5-8.

17. The vial of claim 14 wherein the pH of the formulation is from 5-7.

18. The vial of claim 17 wherein the pH of the formulation is 6.0.

19. The vial of claim 14 wherein the buffer is histidine, phosphate, Tris, citrate, succinate, or other organic acid.

20. A formulation comprising a lyophilized mixture of huMAb4D5-8 in an amount from 5-40 mg/mL, a sugar in an amount from 10-400 mM, a surfactant in an amount from 0.001-0.5%, and histidine buffer, wherein the pH of the formulation is 6.0.

21. A method of treating HER2 overexpressing breast cancer comprising administering to a patient with the breast cancer a reconstituted formulation comprising recombinant humanized HER2 antibody, wherein the reconstituted formulation has been prepared by reconstituting of claim 1 with a diluent to generate the reconstituted formulation.

22. The method as in claim 21 wherein the pH of the formulation is from 5-7.

23. The method as in claim 22 wherein the pH of the formulation is 6.0.

24. The method as in claim 21 wherein the buffer is histidine, phosphate, Tris, citrate, succinate, or other organic acid.

25. The method as in claim 21 wherein the concentration of the humanized HER2 antibody in the reconstituted formulation is from about 5-50 mg/mL.

26. The method as in claim 25 wherein the concentration of the humanized HER2 antibody in the reconstituted formulation is from about 10-40 mg/mL.

27. The method as in claim 21 wherein the antibody is huMAb4D5-8.

28. The method as in claim 21 wherein the pH of the reconstituted formulation 6.0.

29. The method as in claim 21 wherein the diluent is sterile water.

30. The method as in claim 21 wherein the diluent is bacteriostatic water for injection (BWFI).

* * * * *